US012805899B2

(12) United States Patent
Tada et al.

(10) Patent No.: US 12,805,899 B2
(45) **Date of Patent: *Nov. 24, 2026**

(54) MEDICAL DEVICE

(71) Applicant: TERUMO KABUSHIKI KAISHA, Tokyo (JP)

(72) Inventors: Yuichi Tada, Tokyo (JP); Mizuho Hirao, Sagamihara city (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 192 days.

This patent is subject to a terminal disclaimer.

(21) Appl. No.: 18/441,496

(22) Filed: Feb. 14, 2024

(65) Prior Publication Data

US 2024/0180585 A1 Jun. 6, 2024

Related U.S. Application Data

(63) Continuation of application No. 16/698,051, filed on Nov. 27, 2019, now Pat. No. 11,925,383, which is a (Continued)

(30) Foreign Application Priority Data

May 31, 2017 (JP) ................................ 2017-108745

(51) Int. Cl.
*A61B 17/3207* (2006.01)
*A61B 17/32* (2006.01)

(52) U.S. Cl.
CPC ................ *A61B 17/320758* (2013.01); *A61B 2017/320032* (2013.01); *A61B 2017/320766* (2013.01)

(58) Field of Classification Search
CPC ........... A61B 17/320758; A61B 2017/320032; A61B 2017/320766; A61B 2017/320775; A61B 17/3207
See application file for complete search history.

(56) References Cited

U.S. PATENT DOCUMENTS 5,733,296 A * 3/1998 Rogers ........... A61B 17/320783 606/159
2002/0188307 A1 12/2002 Pintor et al.
(Continued)

FOREIGN PATENT DOCUMENTS

JP 2004508096 A 3/2004
JP 2013146559 A 8/2013
(Continued)

OTHER PUBLICATIONS

International Search Report (PCT/ISA/210) mailed on Aug. 28, 2018, by the Japanese Patent Office as the International Searching Authority for International Application No. PCT/2018/021064.
(Continued)

*Primary Examiner* — Ashley L Fishback
(74) *Attorney, Agent, or Firm* — .Buchanan Ingersoll & Rooney PC

(57) ABSTRACT

A medical device is disclosed that can help prevent a guide wire from coming into contact with a rotating body in the middle of performing a treatment and achieves improvement in the efficiency of cutting an object by the rotating body. The medical device has a sheath that is insertable into a body lumen, a rotatable hollow rotating body that is disposed to protrude toward a distal side of the sheath, and guide wire lumens into which a guide wire is insertable in parallel with the sheath. A distal end surface of the rotating body has a concave-convex cut portion formed only between an inner distal end of the hollow rotating body and an outer periphery of the distal end of the hollow rotating body.

18 Claims, 16 Drawing Sheets

Related U.S. Application Data continuation of application No. PCT/JP2018/021064, filed on May 31, 2018.

(56) References Cited

U.S. PATENT DOCUMENTS

| | | | |
|---|---|---|---|
| 2006/0239982 | A1 | 10/2006 | Simpson |
| 2014/0018833 | A1 | 1/2014 | Zhou et al. |
| 2014/0031844 | A1 | 1/2014 | Kusleika |
| 2017/0065295 | A1 | 3/2017 | Patel et al. |
| 2017/0231657 | A1 | 8/2017 | Tada et al. |
| 2019/0192185 | A1 | 6/2019 | Tada et al. |
| 2020/0093510 | A1 | 3/2020 | Tada et al. |

FOREIGN PATENT DOCUMENTS

| | | | | |
|---|---|---|---|---|
| JP | 2014533147 | A | 12/2014 | |
| WO | 2017141924 | A1 | 8/2017 | |
| WO | 2018043290 | A1 | 3/2018 | |
| WO | WO-2018191227 | A1 * | 10/2018 | ............. A61B 17/22 |

OTHER PUBLICATIONS

Written Opinion (PCT/ISA/237) mailed on Aug. 28, 2018, by the Japanese Patent Office as the International Searching Authority for International Application No. PCT/2018/021064.

An English Translation of the International Search Report (Form PCT/ISA/210) and the Written Opinion of the International Searching Authority (Form PCT/ISA/237) issued on Aug. 28, 2018, by the Japanese Patent Office in corresponding International Application No. PCT/JP2018/021064 (17 pages).

* cited by examiner

MEDICAL DEVICE

CROSS-REFERENCES TO RELATED APPLICATIONS

This application is a continuation U.S. application Ser. No. 16/698,051 filed on Nov. 27, 2019, which is a continuation of International Application No. PCT/JP2018/021064 filed on May 31, 2018, which claims priority to Japanese Application No. 2017-108745 filed on May 31, 2017, the entire content of all three of which is incorporated herein by reference.

TECHNICAL FIELD

The present disclosure generally relates to a medical device.

BACKGROUND ART

As a method of treating a stenosed site formed in a blood vessel such as a coronary artery, a treatment using a balloon catheter or a stent placement technique can be performed. However, it can be difficult to obtain effective long-term treatment simply by widening a vascular lumen by means of a balloon, and the placement of a stent can be a cause of new stenosis. In particular, in a complex lesion, such as where plaque in a stenosed site is calcified and hardened or where a stenosed site is generated in a bifurcated portion of a blood vessel, an effective treatment cannot be obtained in some cases simply by performing a treatment using a balloon catheter or stent. For this reason, as a treatment contributing to the extension of a blood vessel patency period or the improvement in complex lesion treatment results, an atherectomy that removes (or excises) an object which is a cause of stenosis, such as plaque, a calcified lesion, and a thrombus, can be desirable.

For example, an atherectomy device that has a long catheter main body and a rotatable rotor unit which is disposed on a distal side of the catheter main body is disclosed in JP-T-2014-533147. In addition, the atherectomy device is configured as what is called an over-the-wire catheter into which a guide wire is inserted over a substantially full length in an axial direction which includes the catheter main body and the rotor unit.

In a case of performing a treatment using the atherectomy device, the efficiency of cutting can depend on properties of an object which is a cutting target formed in a body lumen. For example, in treatment of a mixed lesion including a soft tissue and a hard tissue, if a rotating body (corresponds to the rotor unit) has a structure that can respond to properties of only one tissue, it can be difficult to smoothly cut the object. For this reason, a cutting performance that the efficiency of cutting does not significantly depend on the properties of the object is required for the rotating body.

On the other hand, since the atherectomy device disclosed in JP-T-2014-533147 has the over-the-wire structure as described above, the guide wire is inserted into the rotor unit when performing a treatment. In addition, since the guide wire is inserted into the rotor unit and is guided to a distal side of the rotor unit, the guide wire is likely to come into contact with the rotor unit during the treatment. For this reason, for example, when structural features are added to the rotor unit in order to achieve improvement in the cutting performance of the rotor unit, it can be difficult for the over-the-wire atherectomy device to sufficiently achieve the protection of the guide wire, and a possibility of resulting in damage to the guide wire during the treatment can increase.

SUMMARY

A medical device is disclosed that can help prevent a guide wire from coming into contact with a rotating body during a treatment and can help improve the efficiency of cutting an object by the rotating body.

According to an aspect of the present disclosure, a medical device is disclosed for removing an object that exists in a body lumen. The medical device includes a sheath that is insertable into the body lumen, a rotatable hollow rotating body that is disposed to protrude toward a distal side of the sheath, and a guide wire lumen into which a guide wire is insertable in parallel with the sheath. A distal surface of the rotating body has a corrugated portion.

In accordance with an aspect, a medical device is disclosed for removing an object that exists in a body lumen, the medical device comprising: a sheath insertable into the body lumen; a drive shaft having a distal portion and a proximal portion, the drive shaft configured to extend through the sheath; a rotatable hollow rotating body located on the distal portion of the drive shaft, and wherein a distal surface of the rotating body has a corrugated portion; and a guide wire lumen into which a guide wire is insertable in parallel with the sheath, the guide wire lumen being located on an outer surface of the sheath.

In accordance with another aspect, a medical device is disclosed for removing an object that exists in a body lumen, the medical device comprising: a sheath insertable into the body lumen; a drive shaft having a distal portion and a proximal portion, the drive shaft configured to extend through the sheath; a rotatable hollow rotating body located on the distal portion of the drive shaft, and wherein a distal surface of the rotating body has a severing portion, the severing portion includes a plurality of edge surfaces arranged to be twisted in a circumferential direction of the rotating body on the distal surface of the rotating body; and a guide wire lumen configured to receive a guide wire, the guide wire lumen being parallel to the sheath and arranged on an outer surface of the sheath.

In accordance with an aspect, a medical device is disclosed for removing an object that exists in a body lumen, the medical device comprising: a sheath insertable into the body lumen; a drive shaft having a distal portion and a proximal portion, the drive shaft configured to extend through the sheath; a rotatable hollow rotating body located on the distal portion of the drive shaft, and wherein a distal surface of the rotating body has a severing portion, the severing portion includes a plurality of edge surfaces arranged to be twisted in a circumferential direction of the rotating body on the distal surface of the rotating body; and a twisted direction of the plurality of edge surfaces is the same as a rotation direction of rotatable hollow rotating body.

In accordance with another aspect, a medical device is disclosed for removing an object that exists in a body lumen, the medical device comprising: a sheath configured to be inserted into the body lumen; a drive shaft having a distal portion and a proximal portion, the drive shaft configured to extend through the sheath; a rotatable hollow rotating body located on the distal portion of the drive shaft, and wherein a distal end surface of the rotating body has a concave-convex cut portion formed only between an inner distal end of the hollow rotating body and an outer periphery of the distal end of the hollow rotating body; and a guide wire lumen into which a guide wire is insertable in parallel with the sheath, the guide wire lumen being located on an outer surface of the sheath.

In accordance with an aspect, a medical device is disclosed for removing an object that exists in a body lumen, the medical device comprising: a sheath configured to be inserted into the body lumen; a drive shaft having a distal portion and a proximal portion, the drive shaft configured to extend through the sheath; and a rotatable hollow rotating body located on the distal portion of the drive shaft, and wherein a distal end surface of the rotating body includes a severing portion is formed between an inner circumference of the rotating body and an outer circumference of the rotating body, the severing portion including at least two different tapered portions, and each of the at least two different tapered portions includes a tapered portion on a distal side having an angle with respect to an axis in a longitudinal direction that is greater than an angle with respect to the axis in the longitudinal direction of a tapered portion on a proximal side.

In accordance with another aspect, a medical device is disclosed for removing an object that exists in a body lumen, the medical device comprising: a sheath configured to be inserted into the body lumen; a drive shaft having a distal portion and a proximal portion, the drive shaft configured to extend through the sheath; a rotatable hollow rotating body located on the distal portion of the drive shaft, and wherein a distal end surface of the rotating body has a severing portion, the severing portion includes a plurality of concave-convex shaped notches arranged to be twisted in a circumferential direction of the rotating body on the distal end surface of the rotating body; and a guide wire lumen configured to receive a guide wire, the guide wire lumen being parallel to the sheath and arranged on an outer surface of the sheath.

Even in a case where an object, which is a cutting target, is a mixed lesion, the medical device can perform cutting of the object with relatively high efficiency with the corrugated portion that is formed on the distal surface of the rotating body. In addition, since the medical device is configured as a so-called rapid exchange type device, in which a guide wire insertion portion into which the guide wire is insertable is disposed on the distal side of the sheath, the guide wire can be prevented from coming into contact with the rotating body during the treatment compared to an over-the-wire type device. Accordingly, the medical device can help prevent the occurrence of damage to the guide wire.

DESCRIPTION OF EMBODIMENTS

Set forth below with reference to the accompanying drawings is a detailed description of embodiments of a medical device representing examples of the inventive medical device disclosed here. The dimensions or scales on the drawings may be exaggerated or different from actuality/reality for convenience of description and illustration.

Figure 3:
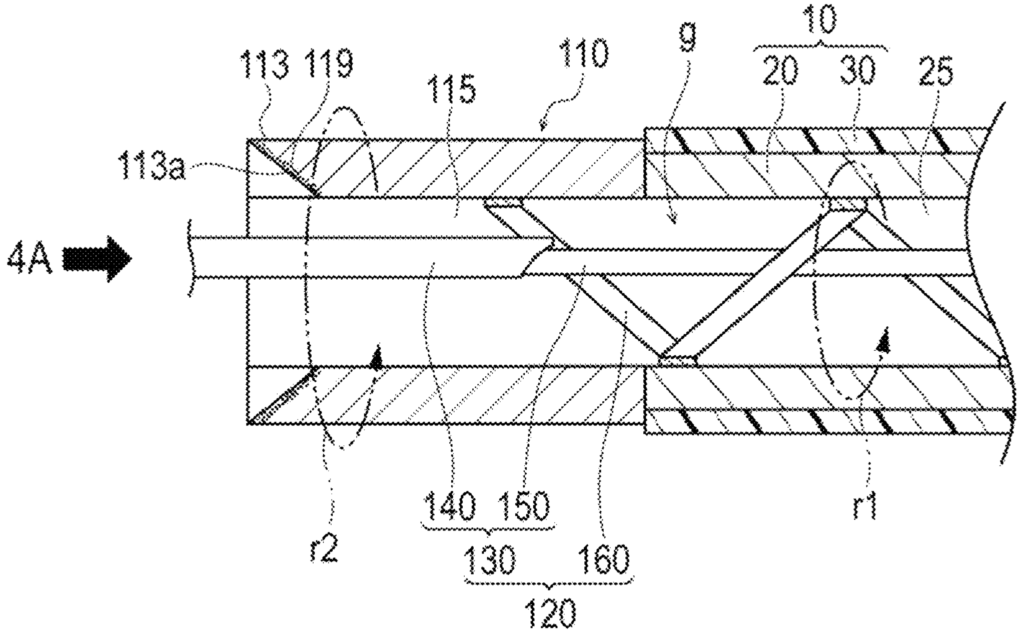
FIG. 3 is a simplified cross-sectional view of a configuration of the distal portion of the medical device according to the embodiment.
Figure 4:
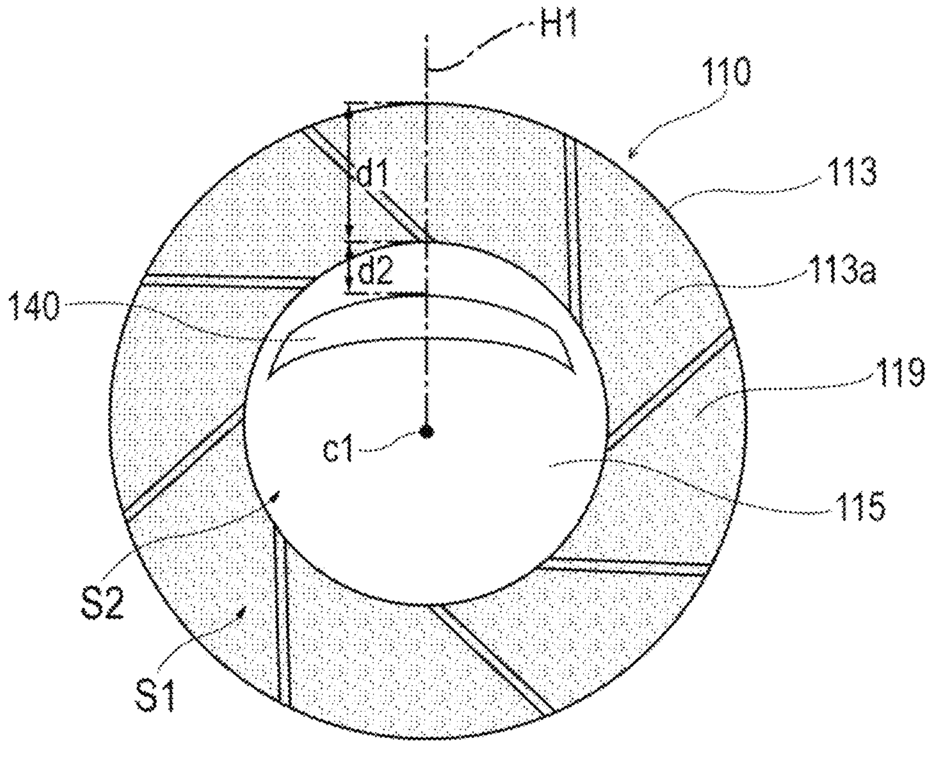
FIG. 4 is a view obtained by simplifying a front view seen from an arrow 4A direction of FIG. 3.
Figure 5:
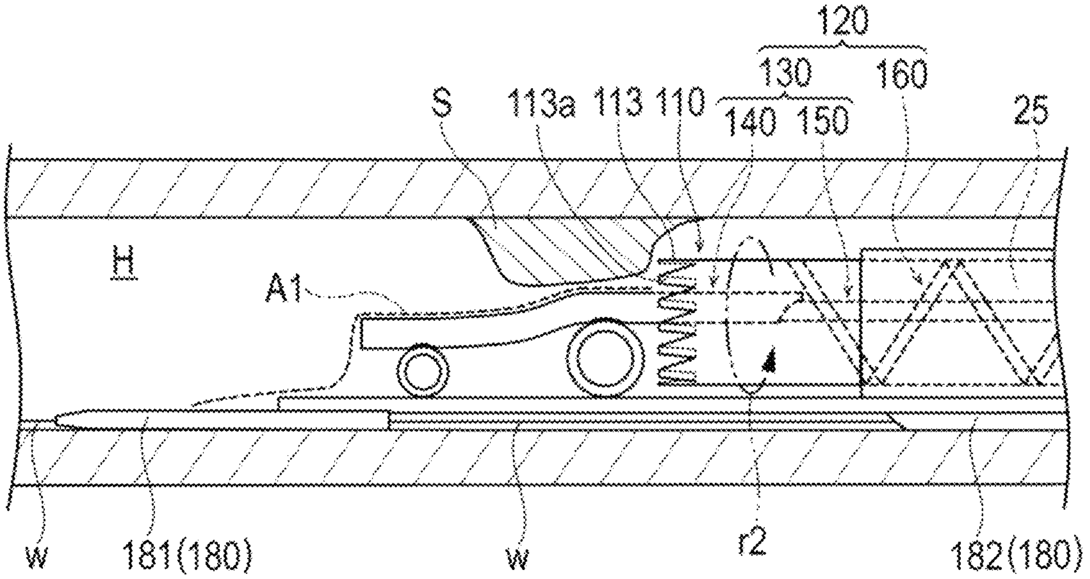
FIG. 5 is a cross-sectional view schematically illustrating a usage example of the medical device according to the embodiment.
Figure 6:
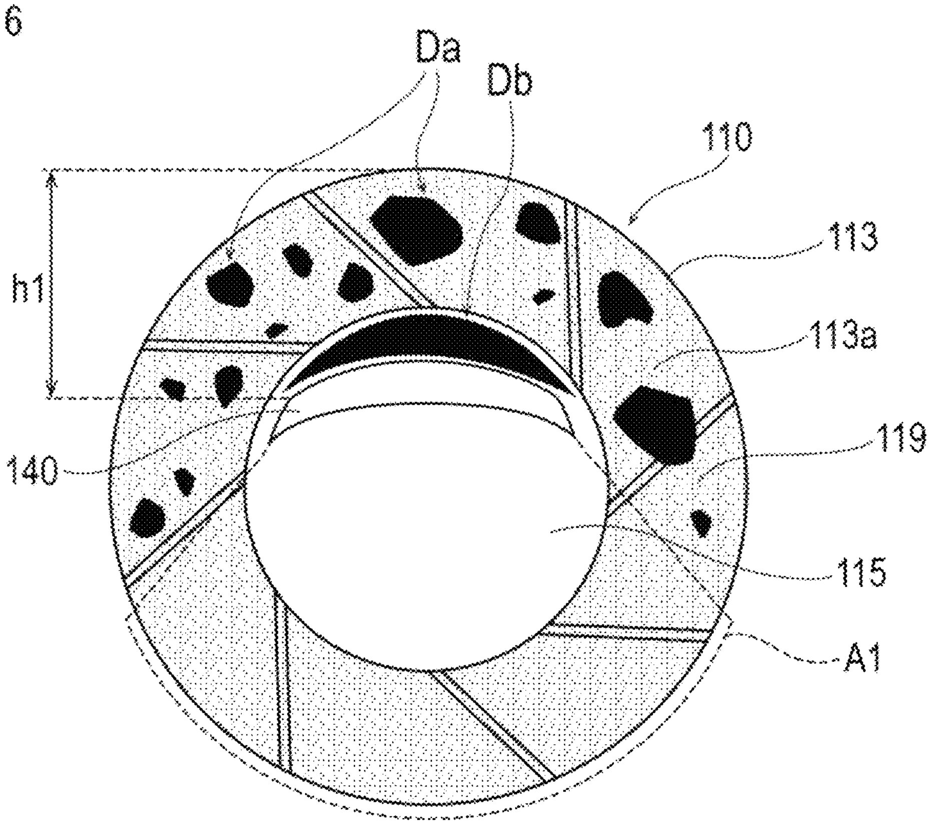
FIG. 6 is a view illustrating an effect of action of the medical device according to the embodiment.

FIGS. 1 to 4 are views for describing a configuration of each portion of a medical device 1 according to the embodiment, and FIGS. 5 and 6 are views for describing action of the medical device 1.

As illustrated in FIG. 5, the medical device 1 according to the embodiment can be a medical jig that can be used in a treatment of cutting an object such as a stenosed site S or an obstructive part formed in a blood vessel H, which is a body lumen.

Figure 1:
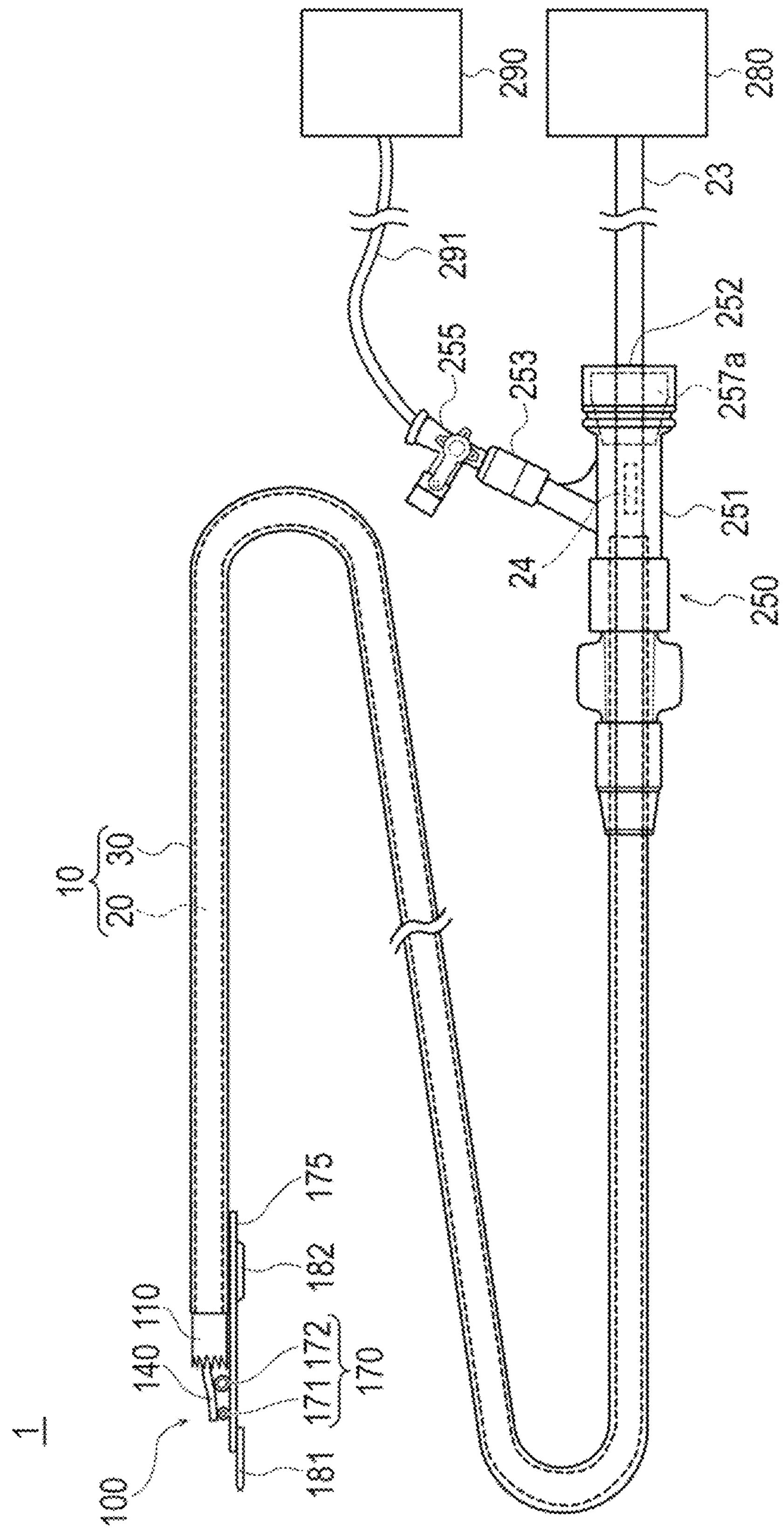
FIG. 1 is a view illustrating a medical device according to an embodiment.

As illustrated in FIG. 1, the medical device 1 can include a sheath 10 that can be inserted into a living body, a distal structure 100 disposed on a distal side of the sheath 10, and a hand operation unit 250 disposed on a proximal side of the sheath 10.

The distal structure 100 will be described.

Figure 2:
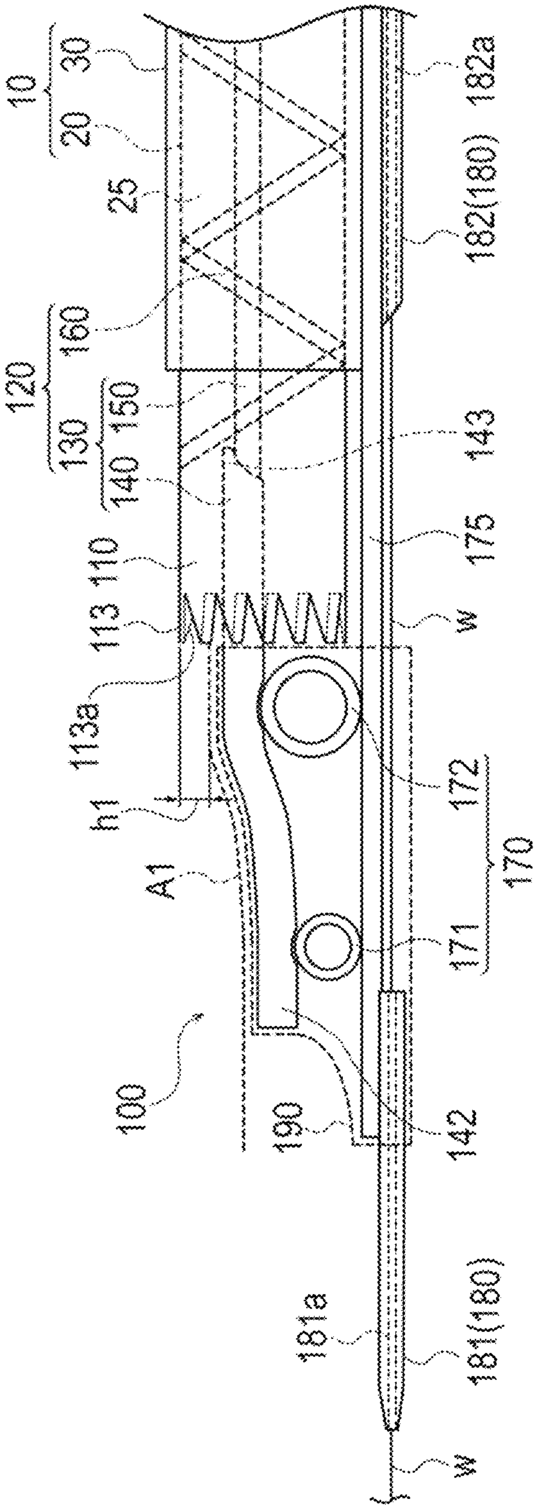
FIG. 2 is an enlarged side view of a distal portion of the medical device according to the embodiment.

FIG. 2 is a side view of a vicinity of a distal portion of the sheath 10, FIG. 3 is a cross-sectional view (longitudinal cross section along an axial direction) of the vicinity of the distal portion of the sheath 10, and FIG. 4 is a plan view seen from a direction indicated with an arrow 4A in FIG. 3. Note that the illustration of some members (a supporting unit 170, a connection section 175, a guide wire insertion portion 180, and a covering member 190) is omitted in FIGS. 3 and 4.

In the disclosure, a side of the medical device 1, which is inserted into the blood vessel H, will be referred to as a distal side, and a side where the hand operation unit 250 is disposed will be referred to as a proximal side. In addition, an extending direction of the sheath 10 will be referred to as the axial direction.

As illustrated in FIG. 2, the distal structure 100 has a rotating body 110 configured to protrude toward the distal side of the sheath 10 and a transporting unit 120 that performs breaking (severing) and transporting of an object (for example, debris or a floating thrombus which is generated through a treatment of a stenosed site), which is a transporting target, in a lumen 25 of the sheath 10.

In accordance with an exemplary embodiment, as illustrated in FIG. 3, the rotating body 110 has a hollow shape including a lumen 115 extending in the axial direction. A severing portion (corresponds to a "corrugated portion") 113 that applies a cutting force to the stenosed site S is formed in a distal portion of the rotating body 110. An opening portion that communicates with the lumen 115 is formed in each of a distal end of the rotating body 110 and a proximal end of the rotating body 110.

Figure 7:
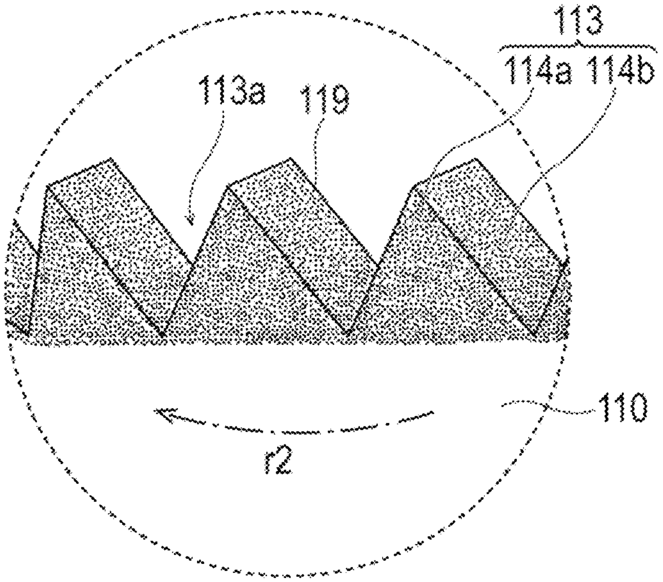
FIG. 7 is an enlarged perspective view of a severing portion and an abrasive portion of a rotating body according to the embodiment.

As illustrated in FIGS. 3 and 7, the severing portion 113 of the rotating body 110 is formed in a corrugated shape notched to a distal side (saw shape). In accordance with an exemplary embodiment, by the severing portion 113 being formed in the distal portion of the rotating body 110, a distal surface 113*a* is formed in a corrugated shape to the distal side. As illustrated in FIG. 4, a plurality of edge surfaces arranged to be twisted in a circumferential direction of the rotating body 110 is formed on the distal surface 113*a*.

As illustrated in FIG. 7, the severing portion 113 has a convex portion 114*a* that tapers off to the distal side (an upper side in FIG. 7) and a concave portion 114*b* that is connected to the convex portion 114*a* and is notched in a concave shape to a proximal side. As illustrated in FIGS. 5 and 6, the severing portion 113 is formed between an inner circumference of the rotating body 110 and an outer circumference of the rotating body 110. That is, the severing portion 113 is formed integrally with the rotating body 110. The portions that form the corrugated shape of the severing portion 113 are regularly arranged along the circumferential direction of the rotating body 110.

As illustrated in FIGS. 4 and 7, an abrasive portion (corresponding to the "corrugated portion") 119 can be provided on the distal surface 113*a* of the severing portion 113. A range (area) where an abrasive portion 119 is formed on the distal surface 113*a* of the rotating body 110 is not particularly limited. However, from a perspective of improvement in the efficiency of cutting by the rotating body 110, for example, it can be preferable for the abrasive portion 119 to be formed over substantially the entire distal surface 113*a*. Note that as illustrated in FIGS. 4 and 7, illustrative dots are attached to a portion of the distal surface 113*a* where the abrasive portion 119 is formed.

In accordance with an exemplary embodiment, the abrasive portion 119 can be provided in the rotating body 110, for example, by making the surface roughness of the distal surface of the rotating body 110 equal to or larger than a predetermined value. For example, the abrasive portion 119 can be formed by subjecting the distal surface 113*a* of the rotating body 110 to diamond electrodeposition, cubic boron nitride (CBN) electrodeposition, ceramic electrodeposition, or other type of processing. However, as will be described later, insofar as predetermined debris Da (refer to FIG. 6) can be formed, a forming method, a structure, or a type of the abrasive portion 119 is not particularly limited. For example, the abrasive portion 119 can be formed by executing surface processing, reforming, and physical polishing onto the distal surface 113*a* of the severing portion 113. Note that for example, any method can be selected according to materials for the rotating body 110 listed below as a specific forming method of the abrasive portion 119.

In accordance with an exemplary embodiment, the rotating body 110 can be made of, for example, a metal material, a resin material, or ceramics with biocompatibility. For example, stainless steel, nickel titanium (titanium alloy), tungsten, cobalt chromium, titanium, and tungsten carbide can be used as the metal material. Surface treatment, such as nitriding, can be executed onto a surface of each of the disclosed metal materials, and thereby a material having a surface with more improved hardness than a base material can be used. In addition, the severing portion 113 may include, for example, a multi-layered structure having the same or different types of metals disposed in multiple layers. For example, BS (acrylonitrile, butadiene, and a styrene copolymer synthetic resin), polyethylene, polypropylene, nylon, PEEK, polycarbonate, acryl, polyacetal, modified polyphenylene ether, acrylonitrile styrene, and a resin having improved strength by adding an additive such as glass fiber to the resin materials can be used as the resin material.

In accordance with an exemplary embodiment, the rotating body 110 is connected to an elongated member (corresponds to a "drive shaft") 20 as will be described later. The rotating body 110 may be formed integrally with the corrugated portions 113 and 119, or the rotating body 110 and the corrugated portions 113 and 119 may be formed as separate members.

In accordance with an exemplary embodiment, the rotating body 110 can be formed such that an area S1 occupied by the distal surface 113*a* is larger than an area S2 occupied by the hollow lumen 115 when seen from the front as illustrated in FIG. 4. By forming the area S1 (a thickness d1 of the distal surface 113*a*) to be relatively large, an area where the distal surface 113*a* and the stenosed site S are in contact with each other can also be relatively large. Therefore, it is relatively easy for the rotating body 110 to generate (i.e., form) the debris Da to be described later (refer to FIG. 6).

Note that in a case where a distal member 140 is disposed in the lumen 115 of the rotating body 110, for example, the thickness d1 of the rotating body 110 along a perpendicular line H1 passing through a central position c1 of the rotating body 110 can be formed to be larger than a size d2 of a clearance between the distal member 140 and the rotating body 110 as illustrated in FIG. 4. By setting each of the dimensions d1 and d2 in this manner, it can be relatively easy to form the debris Da as described above.

Specific sizes or an area ratio between the respective areas S1 and S2 and a size of each of the dimensions d1 and d2 are not particularly limited, and can be set to any value. However, it can be preferable, for example, to set an area ratio between the respective areas S1 and S2 to a value within a range that allows cut debris to flow into the lumen 115 of the rotating body 110 and makes a desired aspiration pressure possible to be applied to the lumen 115 of the rotating body 110.

For example, a volume of the concave portion 114*b* of the severing portion 113 (a volume of a space formed between the adjacent convex portions 114*a*) can be made smaller than a volume of a space between the rotating body 110 and the distal member 140 (refer to FIG. 4) when seen from the front.

As illustrated in FIGS. 2 and 3, the transporting unit 120 has an insertion member 130 that is inserted in the lumen 115 of the rotating body 110 and the lumen 25 of the sheath 10 (the elongated member 20) and a breaking member 160 disposed (i.e., located) around the insertion member 130.

The insertion member 130 has the distal member 140, which forms a distal portion of the insertion member 130 and a proximal member 150, which forms a proximal portion of the insertion member 130.

As illustrated in FIG. 2, a distal portion 142 of the distal member 140 protrudes from a distal side of the rotating body 110. In addition, a proximal portion 143 of the distal member 140 is disposed (i.e., located) in the lumen 115 of the rotating body 110. As illustrated in FIG. 4, for example, a distal surface of the distal member 140 can be formed in a shape having a shape seen from the front that is curved in a crescent shape (i.e., a shape having a middle portion that has the largest area and an area that gradually decreases from the middle portion to both end portions, when seen from the front).

As illustrated in FIG. 3, the breaking member 160 helically extends around the insertion member 130. In accordance with an exemplary embodiment, a distal portion of the breaking member 160 is fixed to an inner surface of the rotating body 110. For example, the distal portion of the breaking member 160 can be formed in a sharp shape. In addition, for example, the distal portion of the breaking member 160 can be formed in a shape like a claw having a distal end bent in a predetermined direction (i.e., a shape that does not go straight to the distal end and is inclined with respect to the axial direction).

The breaking member 160 is disposed such that each of predetermined gaps g is formed between the distal member 140 and the proximal member 150.

In accordance with an exemplary embodiment, the insertion member 130 (the distal member 140 and the proximal member 150) and the breaking member 160 materials are not particularly limited, it is possible to use, for example, each material exemplified as a material for the rotating body 110.

As illustrated in FIG. 3, the sheath 10 has the elongated member 20 and an outer tube shaft 30 that covers the elongated member 20.

In accordance with an exemplary embodiment, the elongated member 20 includes a metal tubular member that has the lumen 25 extending in the axial direction. In accordance with an exemplary embodiment, a predetermined slit can be formed in the elongated member 20 in order to improve curvature in a body lumen, for example, a blood vessel.

In accordance with an exemplary embodiment, the outer tube shaft 30 is disposed (i.e., configured) to cover an outer surface of the elongated member 20. The outer tube shaft 30 protects biological tissues in a living body from the elongated member 20. In addition, the outer tube shaft 30 helps prevent an object (debris or a floating thrombus) in the lumen 25 of the elongated member 20 from flowing out to the outside of the elongated member 20. As the outer tube shaft 30, for example, a hollow member (tubular member) configured of a known resin material, for example, polyethylene, polypropylene, and a polyamide can be used.

Note that in order to make possible to control (change) an orientation of a distal side of the outer tube shaft 30 by operation of a hand-side (proximal portion side) of the outer tube shaft 30, it is preferable to configure the outer tube shaft 30 to have a torque transmission performance to an extent that the operation is possible.

A structure or a material for the elongated member 20 is not particularly limited insofar as it is possible to transmit a rotational drive force from a proximal side to a distal side of the elongated member 20 (from a hand operation unit 250 side to a rotating body 110 side). For example, the elongated member 20 may also include a resin tube including a single layer or a plurality of layers, a resin tube to which a reinforcement member such as a blade is added, a metal pipe to which spiral processing is executed, or a hollow coil spring that can expand and contract in the axial direction.

In accordance with an exemplary embodiment, the elongated member 20 is fixed to the rotating body 110. In the embodiment, as illustrated in FIG. 3, each of the members 20 and 110 is fixed to each other in a state where a proximal surface of the rotating body 110 and a distal surface of the elongated member 20 are aligned such that a seam between the inner surface of the rotating body 110 and an inner surface of the sheath 10 is flat (smooth). Note that a method, for example, bonding, fusion, and welding as a fixing method can be adopted or determined after considering a material for each of the members 20 and 110.

The elongated member 20 is formed to be rotatable. When the elongated member 20 rotates as shown with an arrow r1 in FIG. 3, the rotating body 110 rotates as shown with an arrow r2 in FIG. 3 in conjunction along with the rotation of the elongated member 20. In addition, when the rotating body 110 rotates, the breaking member 160 rotates in conjunction along with the rotation of the rotating body 110. In accordance with an exemplary embodiment, since the insertion member 130 (the distal member 140 and the proximal member 150) is not fixed (interlocked) to all of the rotating body 110, the elongated member 20, and the breaking member 160, the insertion member does not rotate in conjunction along with the rotation of each of the members 20, 110, and 160. That is, the insertion member 130 is disposed in a non-rotation state.

Next, members other than the rotating body 110 and the transporting unit 120 (the insertion member 130 and the breaking member 160) included in the distal structure 100 will be described with reference to FIG. 2.

In accordance with an exemplary embodiment, the distal structure 100 has the supporting unit 170 that supports the distal portion 142 of the distal member 140, which protrudes from the rotating body 110, the connection section 175 that fixes the supporting unit 170 to the sheath 10, the guide wire insertion portion 180 that is fixed to the connection section 175, and the covering member 190 that integrally connects the distal member 140, the supporting unit 170, and the connection section 175 to each other.

In accordance with an exemplary embodiment, the supporting unit 170 has a first supporting unit 171 and a second supporting unit 172. The first supporting unit 171 is disposed on the distal side of the second supporting unit 172.

In accordance with an exemplary embodiment, the first supporting unit 171 and the second supporting unit 172 each include a cylindrical member extending in a direction intersecting the axial direction. The first supporting unit 171 has an outer diameter smaller than the second supporting unit 172. The distal member 140 can be fixed to each of the supporting units 171 and 172. As a fixing method, a known method, for example, bonding, welding, and soldering, can be adopted.

Due to an outer diameter difference between the first supporting unit 171 and the second supporting unit 172, the distal member 140 can be disposed in a state where the distal portion 142 side is more inclined to a downward side (downward side of FIG. 2) of a height direction than a proximal portion side 143 of the distal member 140.

In accordance with an exemplary embodiment, the connection section 175 is fixed to an outer surface of the sheath 10 (an outer surface of the outer tube shaft 30). In accordance with an exemplary embodiment, the connection section 175 can include a rod-like member that extends substantially linearly.

As illustrated in FIGS. 1 and 2, the medical device 1 can be a rapid exchange type device in which the guide wire insertion portion 180 is disposed on the distal side of the elongated member 20 (in a vicinity of a distal portion of the elongated member 20).

In accordance with an exemplary embodiment, the guide wire insertion portion 180 has a first insertion member 181 disposed on the distal side of the rotating body 110 and a second insertion member 182 disposed on the proximal side of the rotating body 110.

A guide wire lumen 181*a* into which a guide wire is insertable is formed in the first insertion member 181. A distal portion of the first insertion member 181 can have a tapered shape, which tapers toward the distal side (i.e., an outer diameter of the distal portion of the first insertion member 181 tapers towards the distal side).

A guide wire lumen 182*a* into which a guide wire is insertable is formed in the second insertion member 182. In accordance with an exemplary embodiment, a distal portion of the second insertion member 182 can be inclined to an outer surface side of the sheath 10. In addition, a proximal portion of the second insertion member 182 can be inclined to the outer surface side of the sheath 10 (refer to FIG. 1).

The first insertion member 181 and the second insertion member 182 can be fixed to the connection section 175, for example, by bonding and fusion. Each of the insertion members 181 and 182 can be disposed at any position that does not overlap a central axis of the sheath 10 (any position in an outer circumferential direction of the sheath 10) by being fixed to the connection section 175 disposed on the outer surface of the sheath 10. By being disposed between each of the insertion members 181 and 182 and the rotating body 110, the connection section 175 can help prevent contact between each of the insertion members 181 and 182 and the rotating body 110. In addition, by forming a space between each of the insertion members 181 and 182 and the rotating body 110, the connection section 175 can help prevent contact between each of the insertion members 181 and 182 and the rotating body 110. The second insertion member 182 may be directly attached to the sheath 10, for example, without going through the connection section 175. In addition, the length in the axial direction and the connecting position of the connection section 175 are not particularly limited. For example, the connection section 175 may be shorter than the second insertion member 182.

Note that a shape, a length, an outer diameter, an inner diameter, and a material for each of the insertion members 181 and 182 are not particularly limited. In accordance with an exemplary embodiment, a diameter of the distal structure 100 can be made smaller, for example, by disposing each of the insertion members 181 and 182 to extend substantially linearly along the axial direction as illustrated. Accordingly, the insertability (deliverability) of the medical device 1 with respect to the stenosed site S can be improved.

In accordance with an exemplary embodiment, the covering member 190 connects the members 140, 175, and 181 to each other in a state of covering a proximal portion of the first insertion member 181, a distal portion of the connection section 175, and the distal portion 142 of the distal member 140. The covering member 190 may include, for example, a heat-shrinkable tube. In accordance with an exemplary embodiment, the heat-shrinkable tube can be a hollow member made of (i.e. configured of), for example, fluorine-based resins such as an ethylene tetrafluoroethylene (ETFE) copolymer and polytetrafluoroethylene (PTFE), polyolefins such as polyethylene (PE) and polypropylene (PP), polyamides, polyesters, and polyurethane.

Note that a method of connecting the guide wire insertion portion 180 (the first insertion member 181 and the second insertion member 182), the connection section 175, and the distal member 140 to each other is not particularly limited. For example, the guide wire insertion portion 180, the connection section 175, and the distal member 140 can be connected to one another by bonding, welding, soldering, and/or a method by means of a fixing member, for example, such as adhesive tape.

Next, a guide surface A1 formed by the distal member 140 and the supporting unit 170 will be described.

As illustrated in FIG. 2, the guide surface A1 is formed on the distal side of the rotating body 110 by the distal member 140 and the supporting unit 170. In addition, as illustrated in FIG. 6, the distal member 140 and the supporting unit 170 cover (shield) a part of the distal surface 113*a* of the rotating body 110 when the distal structure 100 is seen from the front. Accordingly, a range where the distal surface 113*a* of the rotating body 110 can come into contact with the stenosed site S is limited to a range h1 where the guide surface A1 is not formed (hereinafter, referred to as an "effective cutting range").

In a case where the effective cutting range h1 is set as described above, there are the following advantages.

When cutting the stenosed site S, a practitioner such as a doctor can rotate the rotating body 110 as shown with the arrow r2 in FIG. 5. In addition, the practitioner can bring the severing portion 113 closer to the stenosed site S in a state where the rotating body 110 is rotated, and cuts the stenosed site S. For example, when the rotating body 110 goes beyond the stenosed site S and reaches a blood vessel wall positioned on an upper side in FIG. 5 in the middle of performing such a treatment, the risk of making the severing portion 113 penetrate (pierce) the blood vessel wall can occur. On the contrary, when the range where the severing portion 113 exerts a cutting force is limited to the effective cutting range h1 by the guide surface A1 as described above, the risk of making the severing portion 113 penetrate the blood vessel wall can significantly decrease. In accordance with an exemplary embodiment, the penetration of the blood vessel wall can be more reliably prevented by setting the effective cutting range h1 smaller than the thickness of the blood vessel wall.

Next, the hand operation unit 250 will be described.

As illustrated in FIG. 1, the hand operation unit 250 can include a hub 251, a connector unit 253 provided in the hub 251, and a port 255 provided in the connector unit 253.

In accordance with an exemplary embodiment, a proximal portion 23 of the elongated member 20 can be inserted into the hub 251 to be guided out from a proximal port 252 of the hub 251. A valve body 257*a* that helps prevent leakage of a fluid from the proximal port 252 is disposed in a proximal portion of the hub 251.

A proximal portion of the outer tube shaft 30 that covers the elongated member 20 can be inserted in the hub 251, and can be fixed at a predetermined position in the hub 251. In accordance with an exemplary embodiment, the outer tube shaft 30 is not fixed (interlocked) to the elongated member 20 and the rotating body 110.

In the port provided in the connector unit 253, a flow path through which a fluid can flow is formed. In accordance with an exemplary embodiment, the connector unit 253 can be, for example, a Luer taper connector.

A three-way stopcock for operating the flow of a fluid can be disposed in the port 255. The port 255 can be interlocked with an aspiration device 290, for example, via a tube 291 through which the fluid can flow. The aspiration device 290 can be, for example, a fluid aspiration pump that can generate negative pressure.

In accordance with an exemplary embodiment, the proximal portion of the elongated member 20 can be capable of being connected to an external drive apparatus 280 via, for example, a connector (not illustrated). A drive source, for example, an electric motor can generate a drive force for rotating the elongated member 20 can be included in the external drive apparatus 280.

When the external drive apparatus 280 is operated to exert a rotational force to the elongated member 20, the elongated member 20 rotates as shown with the arrow r1 in FIG. 3. When the elongated member 20 rotates, the rotating body 110 fixed to the distal portion of the elongated member 20 and the breaking member 160 fixed to the rotating body 110 rotate as shown with the arrow r2 in FIG. 3. In accordance with an exemplary embodiment, the outer tube shaft 30 does not rotate even in a case where the elongated member 20 rotates since the outer tube shaft is not fixed to the elongated member 20 and the rotating body 110.

In accordance with an exemplary embodiment, for example, a control unit (not illustrated) can be configured to perform operation control of the external drive apparatus 280 and the aspiration device 290. The control unit may include, for example, a microcomputer including a CPU, a RAM, and a ROM. In addition, for example, the control unit may be mounted on the external drive apparatus 280 or the aspiration device 290, or may be incorporated in another device other than the external drive apparatus 280 and the aspiration device 290 and perform transmission and reception of a control signal between each of the devices 280 and 290 and the control unit in a wired or wireless manner. In addition, the control unit may include electric circuits including a battery and switches and may further include a microcomputer including a CPU, a RAM, and a ROM.

In accordance with an exemplary embodiment, the direction of rotation of the rotating body 110 in various treatments may be either clockwise or counterclockwise. In addition, the clockwise direction and the counterclockwise direction may be switched and the rotating body may be rotated as appropriate.

In order to help prevent an aspiration force from being applied to the proximal side of the proximal portion 23 of the elongated member 20, an obstructive member (not illustrated) that blocks the lumen 25 of the sheath 10 can be disposed in the vicinity of the proximal portion 23 of the elongated member 20. The obstructive member may include, for example, an elastic member.

As illustrated in FIG. 1, a side hole 24 for discharging debris can be provided in a vicinity of a proximal end of the elongated member 20. As will be described later, the medical device 1 transports debris severed by the severing portion 113 of the rotating body 110 to the proximal side of the elongated member 20 through the lumen 115 of the rotating body 110 and the lumen 25 of the elongated member 20. In accordance with an exemplary embodiment, the rotating body 110 and the transporting unit 120 disposed in a vicinity of a distal end of the elongated member 20 transport the debris severed by the severing portion 113 to the proximal side of the elongated member 20 while finely breaking the debris. For this reason, the debris is finely broken while rapidly moving from the rotating body 110 side to an elongated member 20 side. As illustrated in FIG. 2, it can be preferable that a gap which allows the debris to enter is not formed between the outer surface of the elongated member 20 and the outer tube shaft 30. Accordingly, the debris can be introduced to a center of the lumen 25 of the elongated member 20 where the transporting unit 120 is disposed. In addition, as illustrated in FIG. 1, the proximal portion 23 of the elongated member 20 can extend further to the proximal side than a proximal end of the outer tube shaft 30. For this reason, a portion where the side hole 24 of the elongated member 20 is formed can be disposed closer to the proximal side than the proximal end of the outer tube shaft 30. When the aspiration device 290 is operated in order to discharge the debris, a negative pressure can be produced in the hub 251 connected to the aspiration device 290 via the tube 291, the connector unit 253, and the port 255. The debris can be transported to the aspiration device 290 via the side hole 24 of the elongated member 20 and the inside of the hub 251. Although a position where the side hole 24 is formed in the elongated member 20 is not particularly limited insofar as it is possible to transport the debris from the elongated member 20 to the aspiration device 290, it can be preferable, for example, for the side hole 24 to be in a vicinity of a base portion of the connector unit 253 (a portion connected to a main body portion of the hub 251) as illustrated in FIG. 1. Since the side hole 24 and the connector unit 253 are disposed to be close to each other by forming the side hole 24 at such a position, the debris can be smoothly transported from the elongated member 20 to a connector unit 253 side.

In accordance with an exemplary embodiment, the valve body 257*a* disposed inside the hand operation unit 250 can be switched between an open state and a closed state by operating an opener (not illustrated) provided in the hand operation unit 250. For example, a valve body and an opener having the same structures as those used in a Y-connector can be used as the valve body 257*a* and an opener 257*b*. In accordance with an exemplary embodiment, the valve body 257*a* may not include a function of switching between the open state and the closed state.

Next, an example of the procedure of a technique using the medical device 1 will be described with reference to FIGS. 5 and 6.

FIG. 5 schematically illustrates a state when the cutting of the stenosed site S formed in a blood vessel H is performed by using the medical device 1, and FIG. 6 schematically illustrates the distal surface 113*a* of the rotating body 110 in the middle of performing the cutting of the stenosed site S.

In accordance with an exemplary embodiment, a practitioner such as a doctor introduces a guiding sheath (not illustrated) to the vicinity of the stenosed site S in a treatment. The guiding sheath can be delivered to the vicinity of the stenosed site S along a guide wire (not illustrated), and wherein the guide wire has been introduced prior to the introduction of the guiding sheath. In accordance with an exemplary embodiment, the use of the guide wire can be omitted when delivering the guiding sheath.

Next, the practitioner delivers the medical device 1 to the vicinity of the stenosed site S via the guiding sheath. At this time, a guide wire w is inserted into each of the first insertion member 181 and the second insertion member 182. The practitioner can rather smoothly deliver the medical device 1 to the vicinity of the stenosed site S by moving the medical device along the guide wire w in each of the insertion members 181 and 182.

Next, the practitioner pushes the distal surface 113*a* of the rotating body 110 to the stenosed site S while rotating the rotating body 110 as shown with the arrow r2 via operation control of the external drive apparatus 280. In accordance with an exemplary embodiment, the distal surface 113*a* of the rotating body 110 can scrape a stenosis object (for example, plaque or a thrombus) included in the stenosed site S by exerting a cutting force to the stenosed site S.

At this time, the rotating body 110 can exert an impact force to the stenosed site S by bringing the severing portion 113 and the distal surface 113*a* where the abrasive portion 119 is formed into contact with the stenosed site S. Accordingly, as illustrated in FIG. 6, the debris Da, which is a fragment of the stenosed site S, can be formed. In addition, when the distal surface 113*a* enters the stenosed site S, the rotating body 110 can scrape (i.e., push or pull) the stenosed site S along a traveling direction of the rotating body 110. Accordingly, debris Db, which can be a relatively large fragment, can be formed between the inner surface of the rotating body 110 and the distal member 140. As described above, the rotating body 110 can form the debris Da by means of the severing portion 113 and the abrasive portion 119, and can form the debris Db by cutting along with the entrance of the rotating body 110 to the stenosed site S.

In a case where the stenosed site S is formed of relatively hard tissues, the severing portion 113 and the abrasive portion 119 formed on the distal surface 113*a* of the rotating body 110 can efficiently cut (break) the stenosed site S in the treatment using the medical device 1. In accordance with an exemplary embodiment, in a case where the stenosed site S is formed of relatively soft tissues, the stenosed site S can be efficiently cut by a rotation of the rotating body 110 while the severing portion 113 bites into the stenosed site S is formed of relatively soft tissues. Also in a case where the medical device 1 is used in a treatment of a mixed lesion in which the stenosed site S includes both hard and soft tissues, the medical device 1 can rather efficiently cut the stenosed site S since cutting by the severing portion 113 and the abrasive portion 119 and cutting along with the movement of the rotating body 110 can be simultaneously executed.

Since the guide wire w is inserted into the first insertion member 181 and the second insertion member 182 while cutting by the rotating body 110 is being performed, careless movement is unlikely to occur. For this reason, since a distance between the rotating body 110 and the guide wire w and a position of the guide wire w (a position in an up-and-down direction illustrated in FIG. 5) are kept within a fixed range, the guide wire w can be prevented from becoming close to and coming into contact with the rotating body 110.

In addition, as illustrated in FIG. 6, since the guide surface A1 is formed on the distal side of the rotating body 110, a range where the severing portion 113 of the rotating body 110 can come into contact with a blood vessel wall is limited to the effective cutting range h1. Accordingly, it is possible to significantly decrease a risk of the severing portion 113 penetrating the blood vessel wall.

In accordance with an exemplary embodiment, the distal member 140 can include a plate-shaped member (a member having a shape that spreads in a right-and-left direction on the drawing of FIG. 6). For this reason, as illustrated in FIG. 6, the guide surface A1 having a relatively large area can be formed. Since the distal member 140 has a shape that spreads in a width direction (the right-and-left direction of FIG. 6), the distal member 140 is supported by staying in contact with an inner peripheral surface of the rotating body 110, for example, even when the position of the distal member 140 is shifted, for example, carelessly in an up-and-down (i.e., upward and downward) direction shown in FIG. 6 in the middle of performing a treatment of the stenosed site S. Therefore, a shift in the position of the distal member 140 can be suppressed or reduced.

In accordance with an exemplary embodiment, as illustrated in FIG. 6, the distal member 140 can be formed in a shape curved in a crescent shape. For this reason, the debris Db formed between the rotating body 110 and the distal member 140 is scraped (i.e., pushed or pulled) into a crescent shape (peel shape) having a relatively small thickness between the inner peripheral surface of the rotating body 110 and the distal member 140.

When cutting the stenosed site S with the rotating body 110, for example, the practitioner operates the aspiration device 290 illustrated in FIG. 1 to aspirate the scraped debris Da and Db into the lumen 115 of the rotating body 110. When operating the aspiration device 290 while rotating the rotating body 110, an aspiration force pulling the debris Da and Db increases due to convection induced along with the rotation of the rotating body 110. Therefore, the debris Da and Db rather smoothly moves into the lumen 115 of the rotating body 110.

In accordance with an exemplary embodiment, the debris Da and Db aspirated in the lumen 115 of the rotating body 110 can be sandwiched in the gaps g formed between the breaking member 160 and the distal member 140 (refer to FIG. 3). Then, when the breaking member 160 rotates relatively to the distal member 140 along with the rotation of the rotating body 110, a shearing force can be exerted to the debris Da and Db sandwiched between the breaking member 160 and the distal member 140, and thus the debris Da and Db can be finely broken. In addition, when the breaking member 160 rotates, the debris Da and Db can be transported to the proximal side due to a rotational force applied between the breaking member 160 and the distal member 140.

In a state of being sandwiched in the gaps g between the distal member 140 and the breaking member 160 and the gaps g between the proximal member 150 and the breaking member 160, the debris Da and Db can be transported to the proximal side of the lumen 25 via each of the gaps g while being shorn (or cut) with the rotation of the breaking member 160. Accordingly, the debris Da and Db can be prevented from clogging the lumen 25, and the debris Da and Db can be rather smoothly transported to a proximal portion side of the sheath 10 (the hand operation unit 250 side).

As described above, in a treatment method according to the embodiment, the debris Da is formed using the corrugated portion (the severing portion 113 and/or the abrasive portion 119) formed on the distal surface 113*a* of the rotating body 110, and the debris Db is formed by cutting along with the movement of the rotating body 110 (entrance to the stenosed site S).

Figure 8:
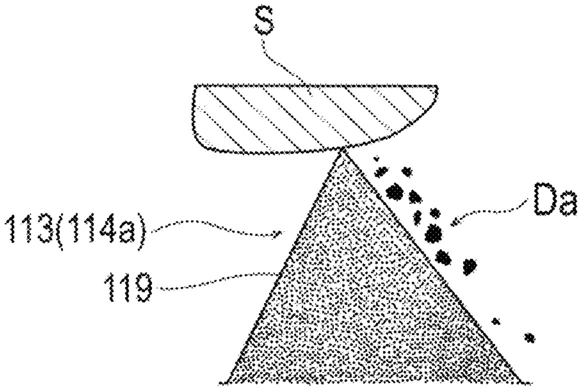
FIG. 8 is a cross-sectional view schematically illustrating a state when the medical device grinds a stenosed site.
Figure 9:
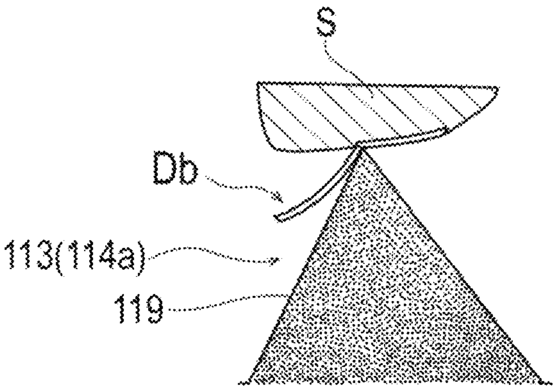
FIG. 9 is a cross-sectional view schematically illustrating a state when the medical device severs the stenosed site.
Figure 10:
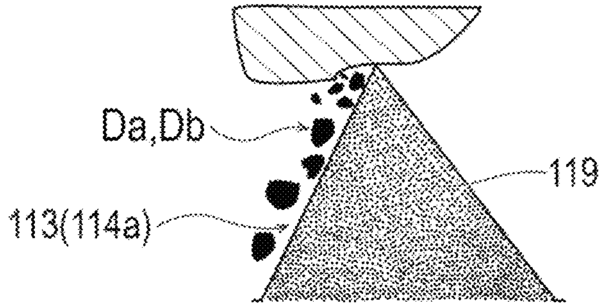
FIG. 10 is a cross-sectional view schematically illustrating a state when the medical device breaks the stenosed site.

In the treatment method, "excising" means removing a part of the stenosed site S from the stenosed site. In addition, the excising means grinding of the stenosed site S by the abrasive portion 119 (refer to FIG. 8), digging and severing of the stenosed site S by the severing portion 113 (refer to FIG. 9), breaking of the stenosed site S or a part of the ground or severed stenosed site S by colliding with the corrugated portion (the severing portion 113) due to the rotation of the rotating body 110 (refer to FIG. 10), or a combination of grinding, digging and severing, and/or breaking.

In addition, in a case where the severing portion 113 has a corrugated shape and the severing portion 113 has the abrasive portion 119 (refer to FIG. 7), the severing portion 113 digs and severs a soft tissue portion of a mixed lesion while the abrasive portion 119 grinds a hard tissue portion of the mixed lesion. After then, the concave portion 114*b* of the severing portion 113 collides with the stenosed site S or a part of the ground or severed stenosed site S due to the rotation of the rotating body 110, and thus the stenosed site can be more finely broken.

In accordance with an exemplary embodiment, for example, the debris Da formed using the abrasive portion 119 grinding the stenosed site S, which is a hard tissue of a mixed lesion, the debris Db formed using the severing portion 113 digging and severing the stenosed site S, which is a soft tissue of the mixed lesion, and debris Da' (not illustrated) formed from breaking caused by collision with the concave portion 114*b* of the severing portion 113 can have sizes satisfying the relation: the debris Db>the debris Da'>the debris Da.

Figure 11:
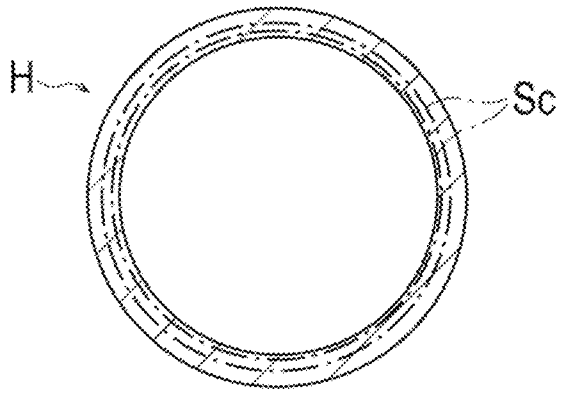
FIG. 11 is a cross-sectional view exemplifying a mixed lesion area.
Figure 12:
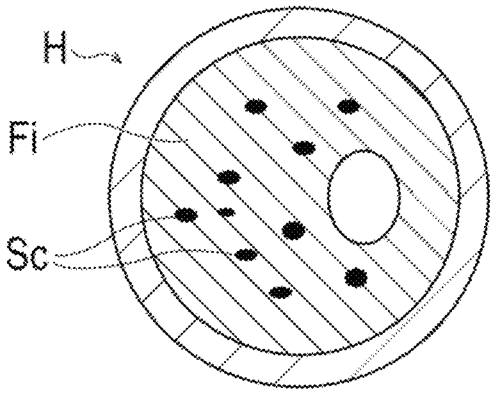
FIG. 12 is a cross-sectional view exemplifying the mixed lesion area.
Figure 13:
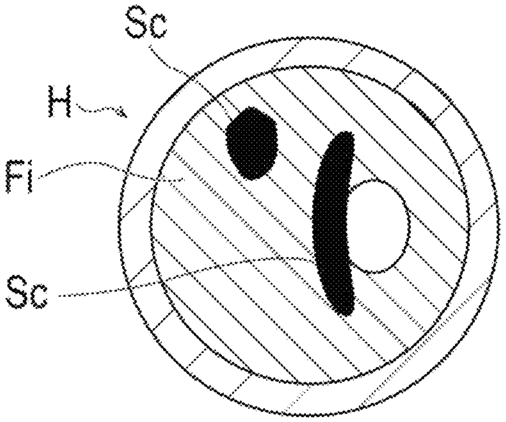
FIG. 13 is a cross-sectional view exemplifying the mixed lesion area.

In addition, the "mixed lesion" in the disclosure means, for example, a lesion in which calcium exists in layers on a wall of the blood vessel H (refer to FIG. 11), a lesion in which fibrous hyperplasia Fi is interspersed with calcium Sc (refer to FIG. 12), and a lesion in which a nodule of calcium Sc exists in the fibrous hyperplasia Fi (refer to FIG. 13).

In addition, in the treatment method, by bringing the severing portion 113 and the distal surface 113*a* where the abrasive portion 119 are formed into contact with the stenosed site S, the rotating body 110 exerts an impact force to pulverize (or crush) the stenosed site S, and thus the debris Da, which is a fragment of the stenosed site S, can be formed.

In addition, in the treatment method, when a mixed lesion including both hard and soft tissues is treated, the rotating body 110 may simultaneously execute cutting along with the movement of the rotating body 110 and cutting using the corrugated portion (the severing portion 113 and/or the abrasive portion 119) formed on the distal surface 113*a* of the rotating body 110.

Next, the action of the medical device 1 according to the embodiment will be described.

The medical device 1 according to the embodiment has the sheath 10 that is insertable into a body lumen such as the blood vessel H, the rotatable hollow rotating body 110 that is disposed to protrude toward the distal side of the sheath 10, the guide wire lumens 181*a* and 182*a* into which the guide wire w is insertable in parallel with the sheath 10. In accordance with an exemplary embodiment, the distal surface 113*a* of the rotating body 110 can have the corrugated portions 113 and 119.

In accordance with an exemplary embodiment, the medical device 1 configured as described above allows the corrugated portions 113 and 119 formed on the distal surface 113*a* of the rotating body 110 to cut the stenosed site S with rather high efficiency even in a case where the stenosed site S as a cutting target is a mixed lesion (i.e., relatively hard tissues and relatively soft tissues). In addition, since the medical device 1 can be a rapid exchange type device, in which the guide wire insertion portion 180 into which the guide wire w is insertable is disposed on the distal side of the sheath 10, the guide wire w can be prevented from coming into contact with the rotating body 110 in the middle of the treatment compared to an over-the-wire type device. Accordingly, the medical device 1 can help prevent the occurrence of damage to the guide wire w.

In addition, the corrugated portions of the medical device 1 include the corrugated severing portion 113 formed at the distal portion of the rotating body 110 and the abrasive portion 119 formed on the distal surface 113*a* of the rotating body 110. For this reason, when cutting the stenosed site S, the medical device 1 can cut the stenosed site S to be pulverized (or crushed) by bringing the distal surface 113*a* of the rotating body 110 into contact with the stenosed site S.

In addition, the guide wire insertion portion 180 of the medical device 1 has the first insertion member 181 disposed on the distal side of the rotating body 110 and the second insertion member 182 disposed on the proximal side of the rotating body 110. For this reason, since careless movement is unlikely to occur by inserting the guide wire w into the first insertion member 181 and the second insertion member 182 while cutting by the rotating body 110 is being performed, the guide wire can be prevented from becoming close to and/or coming into contact with the rotating body 110. Since the first insertion member 181 is disposed on the distal side of the rotating body 110 and the second insertion member 182 is disposed on the proximal side of the rotating body 110, each of the insertion members 181 and 182 can be prevented from coming into contact with the rotating body 110, and the occurrence of damage to each of the insertion members 181 and 182 or damage to the guide wire w can be prevented.

In addition, when seen from the front, that is from the distal side of the rotating body 110, the rotating body 110 of the medical device 1 is formed such that the area occupied by the distal surface 113*a* is larger than the area occupied by the lumen 115 of the rotating body 110. For this reason, an area where the distal surface 113*a* is in contact with the stenosed site S can be relatively large, and thus it is rather easy to form the debris Da, which is a fragment of the stenosed site S.

Next, modification examples of the severing portion will be described.

Figure 14:
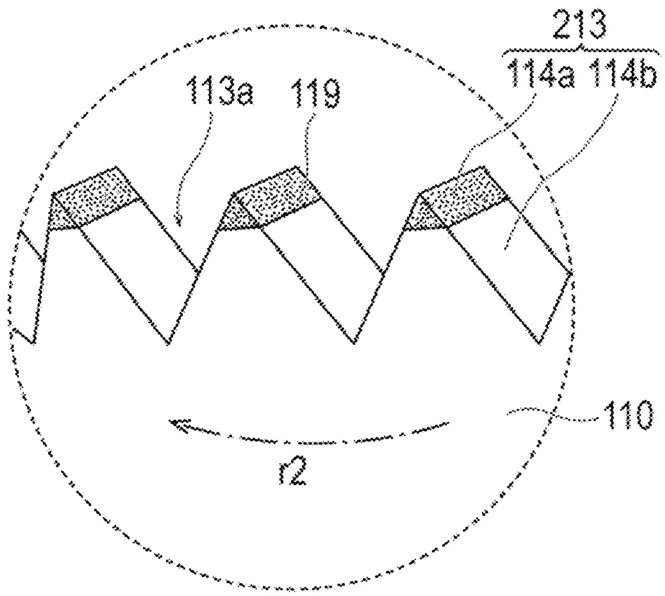
FIG. 14 is an enlarged perspective view of a severing portion and an abrasive portion of a rotating body according to Modification Example 1.

FIG. 14 is a partially enlarged view of a severing portion 213 according to Modification Example 1. For example, the severing portion 213 may be formed such that the abrasive portion 119 is formed only in a vicinity of a distal end of the convex portion 114*a*. Similar to the severing portion 113 according to the aforementioned embodiment, the severing portion 213 configured in this manner digs and severs a soft tissue portion of a mixed lesion, while the abrasive portion 119 grinds a hard tissue portion of the mixed lesion. After then, the concave portion 114*b* of the severing portion 213 collides with the stenosed site S or a part of the ground or severed stenosed site S due to the rotation of the rotating body 110, and thus the stenosed site can be finely broken.

Figure 15:
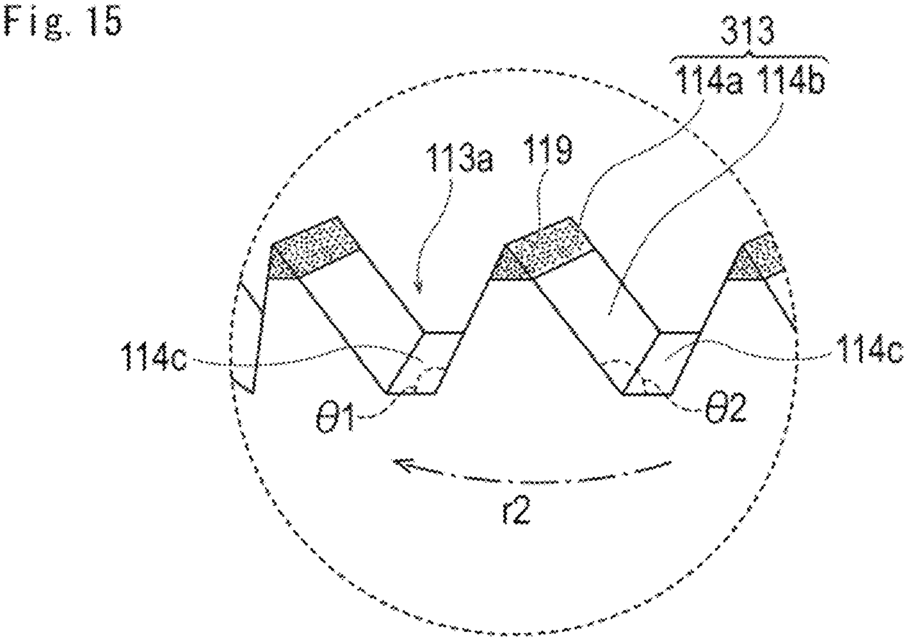
FIG. 15 is an enlarged perspective view of a severing portion and an abrasive portion of a rotating body according to Modification Example 2.

FIG. 15 is a partially enlarged view of a severing portion 313 according to Modification Example 2. The severing portion 313 may have, for example, a flat bottom portion 114*c* between adjacent portions of the corrugated shape. An angle θ1 formed between a corrugated distal surface in the rotation direction of the rotating body 110 (arrow r2 direction) and the bottom portion 114*c* and for example, an angle θ2 formed between a corrugated proximal surface in the rotation direction of the rotating body 110 and the bottom portion 114*c* can be formed to satisfy, for example, a relationship of θ2≥θ1. Note that a size of each of the angles θ1 and θ2 is not particularly limited.

Figure 16:
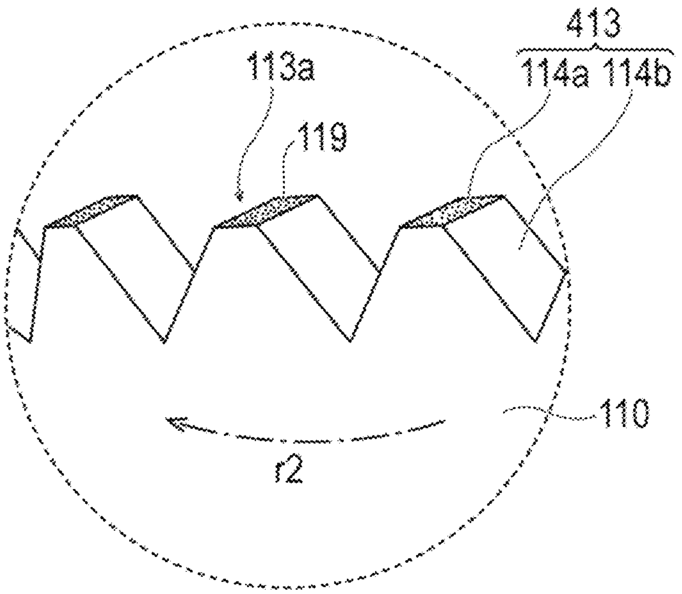
FIG. 16 is an enlarged perspective view of a severing portion and an abrasive portion of a rotating body according to Modification Example 3.

FIG. 16 is a partially enlarged view of a severing portion 413 according to Modification Example 3. A distal end of the convex portion 114*a* of the severing portion 413 can be formed with, for example, a flat surface (or relatively flat surface). By forming the severing portion 413 with a flat or relatively flat surface, it is possible for the distal end of the severing portion 413 to help prevent a blood vessel wall or a guiding sheath inner wall from being damaged.

Figure 17:
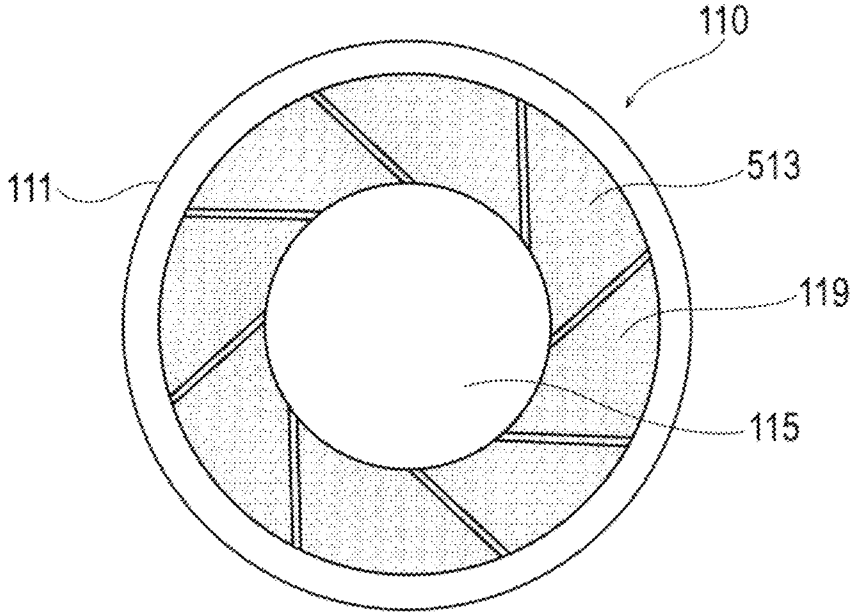
FIG. 17 is an enlarged perspective view of a severing portion and an abrasive portion of a rotating body according to Modification Example 4.

FIG. 17 is an enlarged front view of a severing portion 513 according to Modification Example 4. The severing portion 513 can be formed closer to a rotation center of the rotating body 110 (the center of FIG. 17) than an outer surface portion 111 forming a maximum outer diameter portion of the rotating body 110.

As illustrated in FIG. 2, the medical device 1 has an exposed corrugated severing portion and a rapid exchange structure. Therefore, when inserting and pushing the medical device 1 forward to a body lumen such as the blood vessel H, there is a possibility that a blood vessel wall or the guiding sheath comes into contact with the severing portion of the medical device 1. For example, in a case where the corrugated shape is formed closer to the rotation center of the rotating body 110 than the outer surface portion 111 forming the maximum outer diameter portion of the rotating body 110 as in the severing portion 513 according to the modification example, it is possible to prevent scratches from being left when the severing portion 513 is in contact with a blood vessel wall or the guiding sheath.

Figure 18:
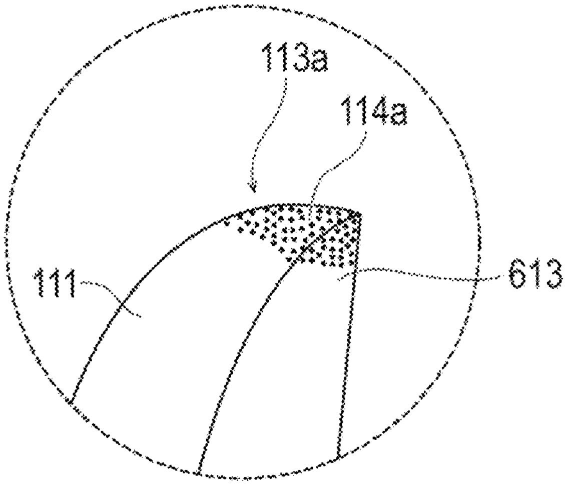
FIG. 18 is an enlarged perspective view of a severing portion and an abrasive portion of a rotating body according to Modification Example 5.

FIG. 18 is a partially enlarged view of a severing portion 613 according to Modification Example 5. The outer surface portion 111 of a distal end of the convex portion 114*a* of the severing portion 613 can include, for example, a curved surface that is gently curved in a convex shape toward an outer side of the rotating body 110 (a surface on which R-processing, for example, a mechanical process, is executed). Even in a case where the distal end of the convex portion 114*a* of the severing portion 613 is in contact with a blood vessel wall or the guiding sheath, the distal end of the convex portion 114*a* of the severing portion 613 formed in that manner can slide from the contact position, so that the blood vessel wall or the guiding sheath inner wall can be protected.

Figure 19:
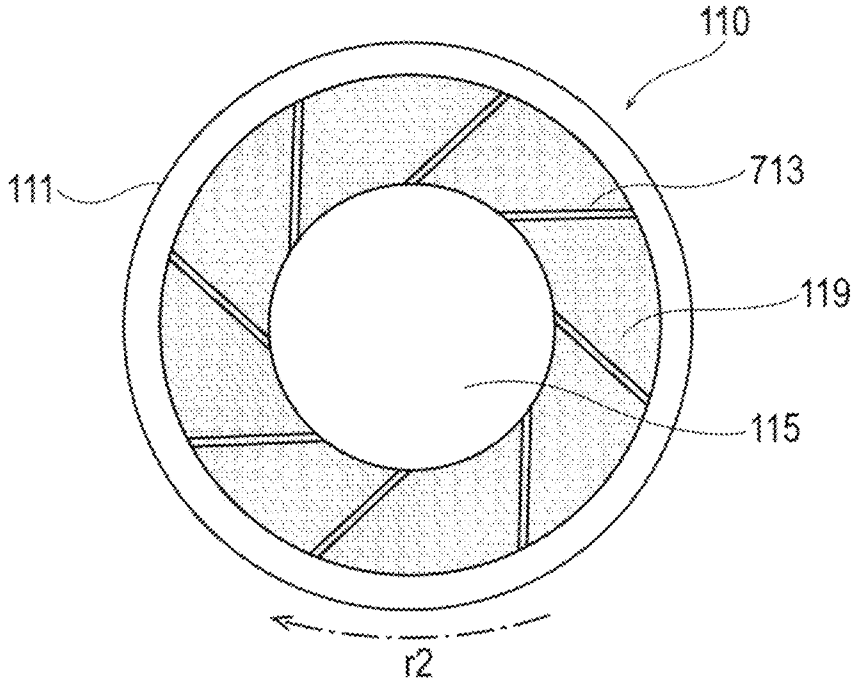
FIG. 19 is a front view illustrating a rotating body according to Modification Example 6.

FIG. 19 is a front view of the rotating body 110 according to Modification Example 6. A direction where edge surfaces of a severing portion 713 included in the rotating body 110 are twisted is an opposite direction to the rotating body 110 according to the aforementioned embodiment (refer to FIG. 4) with the rotation direction of the rotating body 110 (a direction shown with the arrow r2 in FIG. 19) as reference. By the edge surfaces being twisted in the direction described above, it is possible for the rotating body 110 to cut out, for example, a soft tissue with relatively high efficiency.

Figure 20:
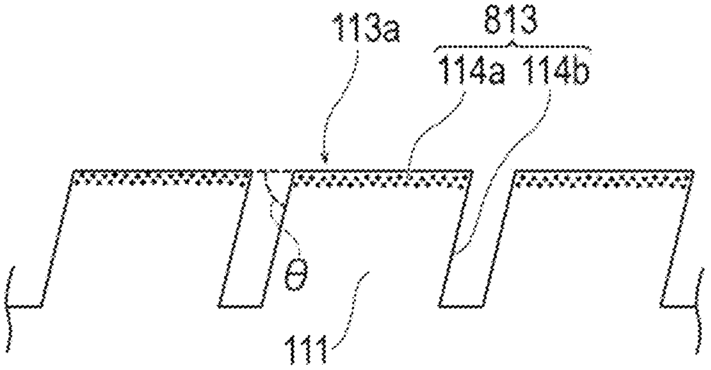
FIG. 20 is an enlarged side view of a severing portion and an abrasive portion of a rotating body according to Modification Example 7.
Figure 21:
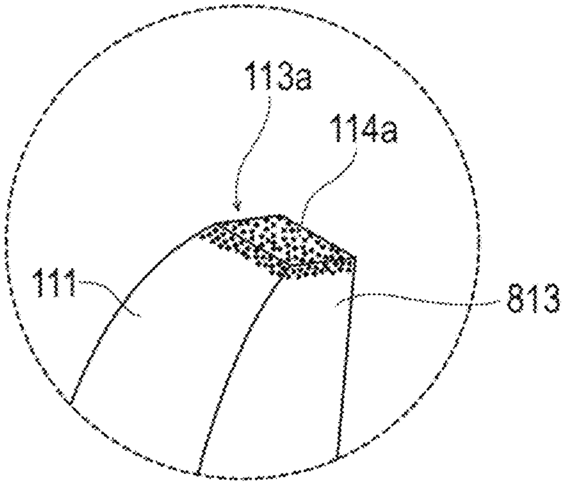
FIG. 21 is an enlarged perspective view of the severing portion and the abrasive portion of the rotating body according to Modification Example 7.

FIG. 20 is a partially enlarged view (side view) of a severing portion 813 according to Modification Example 7, and FIG. 21 is an enlarged perspective view of the severing portion 813. As illustrated in FIG. 20, a distal end of the convex portion 114*a* of the severing portion 813 can be formed with a flat surface. In addition, the severing portion 813 may have, for example, a substantially rectangular shape formed with a predetermined rake angle θ in side view. Note that although a size of the rake angle θ is not particularly limited, it can be preferable, for example, that the rake angle θ is an acute angle.

As illustrated in FIG. 21, the outer surface portion 111 of the severing portion 813 can be formed, for example, with a curved surface that is gently curved in a convex shape toward the outer side of the rotating body 110 (a surface on which R-processing is executed). Even in a case where the distal end of the convex portion 114*a* of the severing portion 813 is in contact with a blood vessel wall or the guiding sheath, the severing portion 813 formed as in the modification example allows protection of the blood vessel wall or the guiding sheath inner wall.

Next, a modification example of a medical device 1A will be described.

Modification Example

Figure 22:
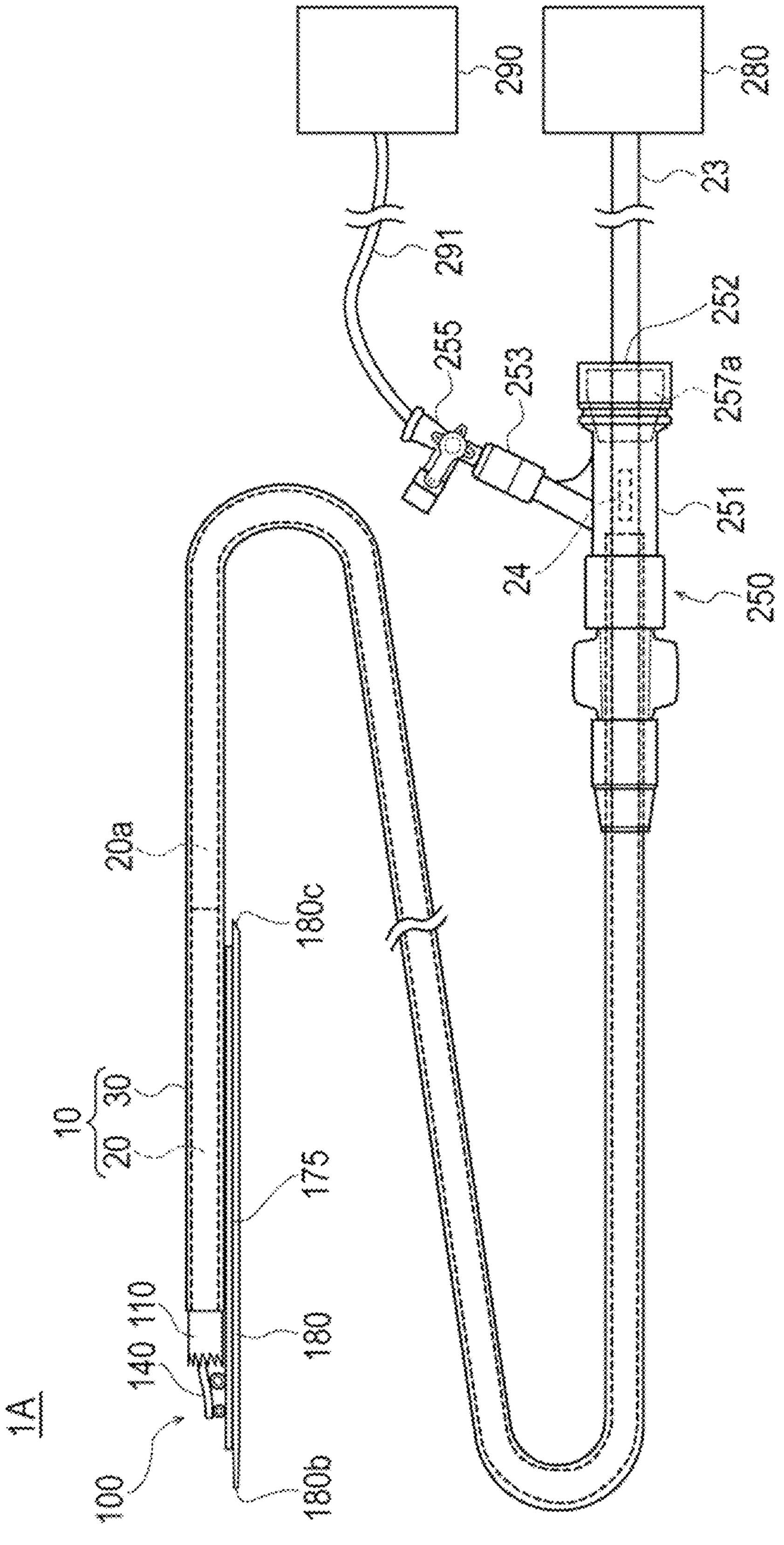
FIG. 22 is a view illustrating a medical device according to a modification example.
Figure 23:
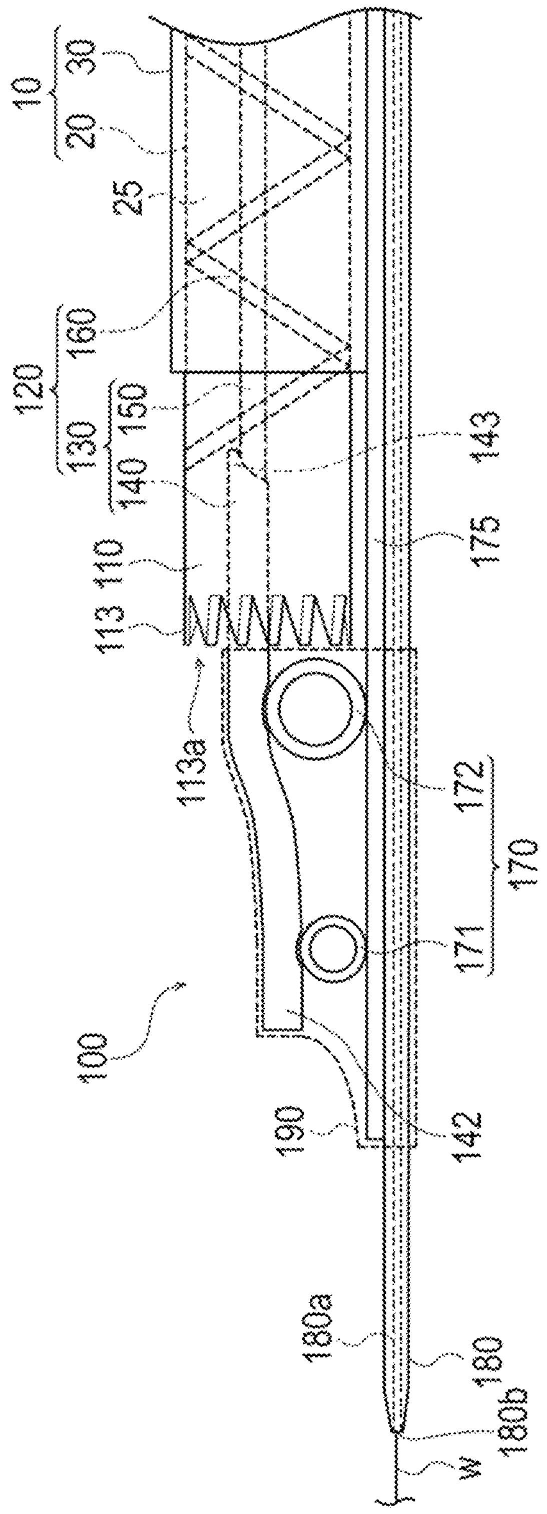
FIG. 23 is an enlarged side view of a distal portion of the medical device according to the modification example.

As illustrated in FIGS. 22 and 23, the guide wire insertion portion 180 can include a guide wire lumen 180*a* formed with, for example, one member continuously extending from the distal side of the rotating body 110 to the proximal side. The guide wire insertion portion 180 can have a length in an axial direction, for example, of 15 mm to 600 mm, and the connection section 175 can have a length in the axial direction, for example, 3 mm to 100 mm.

In a case of configuring the guide wire insertion portion 180 as in the modification example, for example, a distal end opening portion 180*b* of the guide wire insertion portion 180 can be disposed closer to the distal side than the distal surface 113*a* of the rotating body 110 is, and a proximal end opening portion 180*c* of the guide wire insertion portion 180 can be disposed closer to the proximal side than the distal surface of the rotating body 110 is. When each of the opening portions 180*b* and 180*c* of the guide wire insertion portion 180 is disposed as described above, the guide wire w disposed in a vicinity of the distal surface 113*a* of the rotating body 110 is inserted into the guide wire insertion portion 180. Therefore, direct contact with the rotating body 110 can be prevented.

In addition, when the guide wire insertion portion 180 of which a length along the axial direction is relatively large is disposed in the sheath 10 as in the modification example, the pushability of the medical device 1A increases when moving the sheath 10 along the guide wire w.

As illustrated in FIG. 22, for example, in a case where the elongated member 20 forming the sheath 10 includes a relatively flexible hollow member (not illustrated) disposed on the distal side and a relatively hard hollow member 20*a* disposed on a proximal side of the flexible hollow member, the proximal end opening portion 180*c* of the guide wire insertion portion 180 can be disposed on the distal side of a distal end of the hollow member 20*a*. In a case where the guide wire insertion portion 180 is disposed in this manner, the medical device 1A can follow the guide wire w. In addition, for example, the proximal end opening portion 180*c* of the guide wire insertion portion 180 can be disposed on a proximal side of the distal end of the hollow member 20*a*. In a case where the guide wire insertion portion 180 is disposed in this manner, the relatively hard hollow member 20*a* can be moved along the guide wire w, so that the medical device 1A can have increased pushability. In addition, in this case, the guide wire insertion portion 180 can help prevent the occurrence of rupture of the elongated member 20 at a connection portion between the hollow member on the distal side and the hollow member 20*a* on the proximal side.

Note that a material and a length in the axial direction of each of the hollow members configuring the elongated member 20 are not particularly limited.

In accordance with an exemplary embodiment, it is also possible, for example, to configure the guide wire insertion portion with only one of the first insertion member 181 and the second insertion member 182 although description of the only one of the first insertion member 181 and the second member 182 with a drawing is omitted. In a case where the guide wire insertion portion includes one insertion member in this manner, it can be preferable to provide the first insertion member 181 (refer to FIG. 2) disposed on the distal side of the rotating body 110, from a perspective of the deliverability of the medical device 1.

Figure 24:
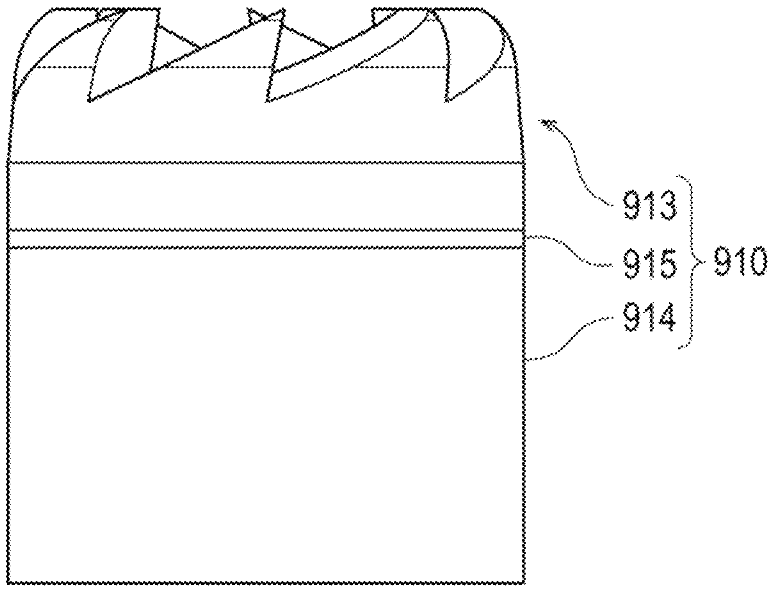
FIG. 24 is a side view illustrating a severing portion of a rotating body according to Modification Example 8.
Figure 25:
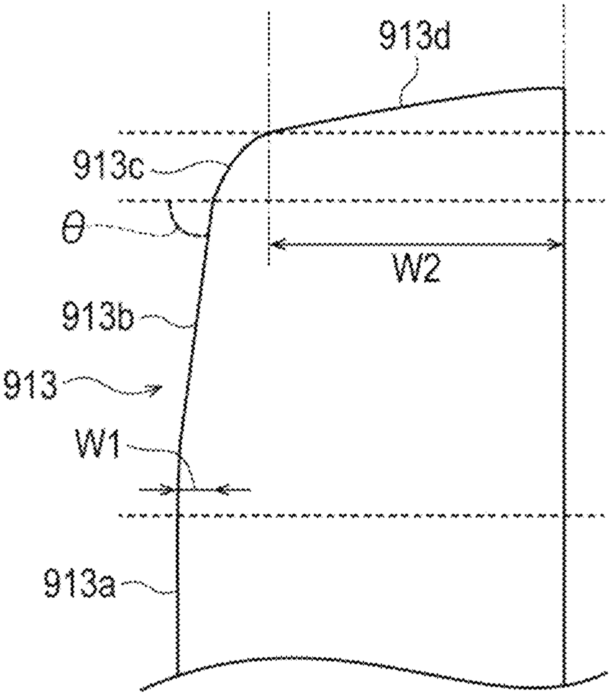
FIG. 25 is an enlarged side view of a part of the severing portion of the rotating body according to Modification Example 8.
Figure 26:
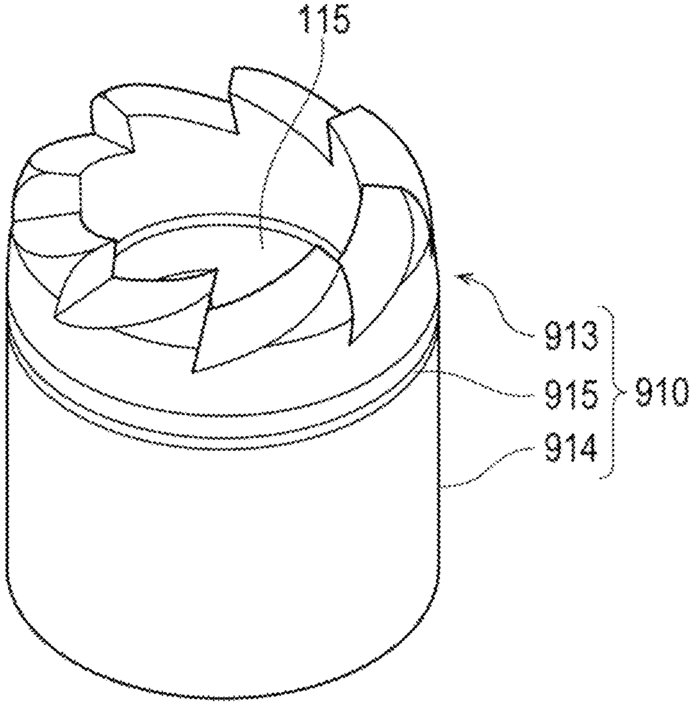
FIG. 26 is a perspective view illustrating the severing portion of the rotating body according to Modification Example 8.

FIGS. 24 to 26 illustrate a rotating body 910 according to Modification Example 8.

As illustrated in FIG. 24, the rotating body 910 has a severing portion 913 on which a corrugated distal surface is formed, a first joint portion 914 formed of the same material as the elongated member (drive shaft) 20, and a second joint portion 915 disposed between the severing portion 913 and the first joint portion 914.

The first joint portion 914 is connected to the elongated member 20. The first joint portion 914 can be formed of a metal, for example, stainless steel (SUS). The first joint portion 914 has good processability by being formed of a metal such as SUS. In addition, the first joint portion can be formed of the same material as the elongated member 20. By forming in this manner, connection with the elongated member 20 can be rather easy. In addition, changing a shape can be rather easy, and it can also be rather easy to improve a torque transmission performance.

The second joint portion 915 can be formed of, for example, silver wax. The second joint portion 915 connects the severing portion 913 to the first joint portion 914.

In accordance with an exemplary embodiment, the severing portion 913 can be formed of a carbide material, for example, tungsten carbide. By selecting a carbide material, the severing portion 913 can be formed to have a hardness greater than (i.e., higher than) a hardness of a calcified lesion area (the stenosed site S).

FIG. 25 is an enlarged side view of a part of the severing portion 913. The severing portion 913 has a straight portion 913*a* that extends substantially linearly from the proximal side to the distal side, a first tapered portion 913*b* that is disposed on a distal side of the straight portion 913*a* and extends in a tapered shape from the proximal side to the distal side, a second tapered portion 913*c* that is disposed on a distal side of the first tapered portion 913*b* and extends in a tapered shape from the proximal side to the distal side, and a third tapered portion 913*d* that is disposed on a distal side of the second tapered portion 913*c* and extends in a curved surface shape from the proximal side to the distal side.

In accordance with an exemplary embodiment, the straight portion 913*a* can be disposed on an outermost circumferential portion of the rotating body 910. When performing a treatment using the medical device, each of the tapered portions 913*b* and 913*d* disposed on an inner side of the straight portion 913*a* can exert a cutting force to a lesion area. Since each of the tapered portions 913*b* and 913*d* has a convex shape gently curved to an outer side of the rotating body 910, a blood vessel wall can be protected even in a case where the rotating body 910 comes into contact with the blood vessel wall. In addition, since the third tapered portion 913*d* protrudes toward the distal side, a cutting force of the severing portion 913 can be improved.

As illustrated in FIG. 25, in accordance with an exemplary embodiment, it can be preferable that a width W1 of the first tapered portion 913*b* be smaller than a width W2 of the third tapered portion 913*d*. For example, because when the width W2 of the third tapered portion 913*d* can be relatively small (i.e., excessively small), a range where the third tapered portion 913*d* exerts a severing force to a lesion area is narrow, and thus a possibility that passing through the lesion area becomes difficult.

In accordance with an exemplary embodiment, it can be preferable for the first tapered portion 913*b* to have, for example, a shape that forms the predetermined rake angle θ when seen from the side as illustrated in FIG. 25. Although the size of the rake angle θ is not particularly limited, it can be preferable, for example, that the rake angle θ is an acute angle.

Figure 27:
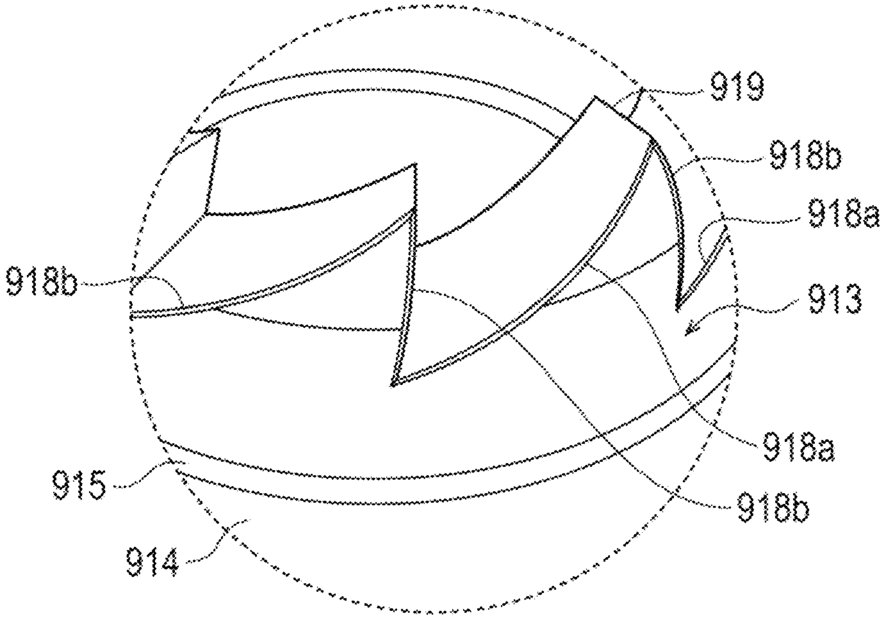
FIG. 27 is an enlarged perspective view of a part of a severing portion of a rotating body according to Modification Example 9.

FIG. 27 illustrates a rotating body according to Modification Example 9.

In the rotating body according to Modification Example 9, edge portions of outer circumferential side surfaces 918*a* and 918*b* of the severing portion 913 are removed (chamfering). By removing the edge portions, it is possible for the rotating body to reduce an effect of the corrugated portion on a blood vessel wall when a distal end of the severing portion 913 is in contact with the blood vessel wall. A distal end 919 of the severing portion 913 can exert a severing force to a lesion area regardless of presence or absence of the edge portions of the outer circumferential side surfaces 918*a* and 918*b*. Note that the processing of removing the edge portions of the outer circumferential side surfaces 918*a* and 918*b* may be performed, for example, onto only one of the outer circumferential side surface 918*a* and the outer circumferential side surface 918*b*.

Figure 28:
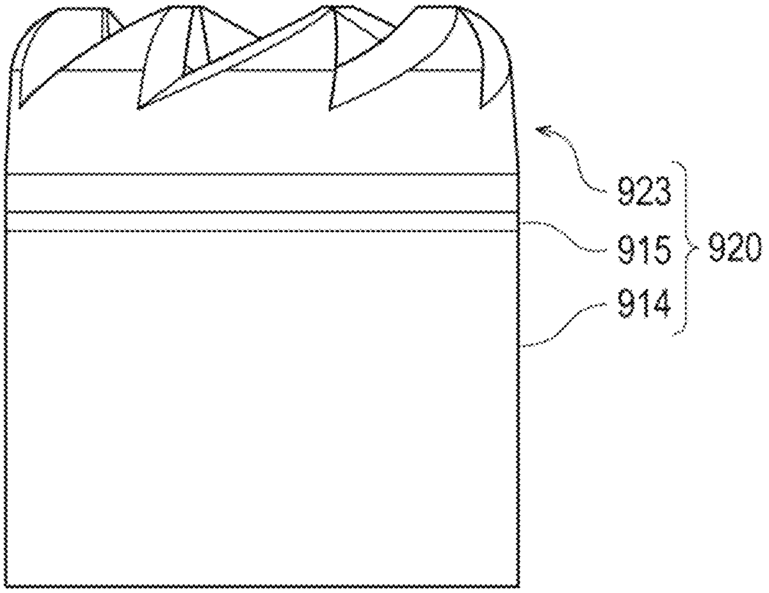
FIG. 28 is a side view illustrating a severing portion of a rotating body according to Modification Example 10.
Figure 29:
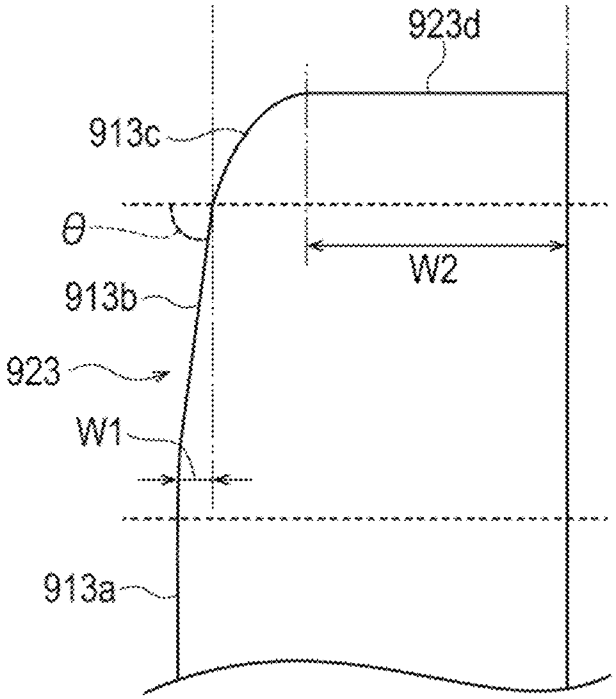
FIG. 29 is an enlarged side view of a part of the severing portion of the rotating body according to Modification Example 10.

FIGS. 28 and 29 illustrate a rotating body 920 according to Modification Example 10.

The rotating body 920 according to Modification Example 10 is different from the rotating body 910 according to Modification Example 8 (refer to FIGS. 24 to 26) in that the third tapered portion 913*d* is not formed. Since other configurations are practically the same as Modification Example 8, description of the configuration will be omitted.

As illustrated in FIG. 29, a distal end 923*d* of a severing portion 923 of the rotating body 920 has a relatively flat linear shape. Compared to the severing portion 913 of the rotating body 910 according to Modification Example 8, the severing portion 923 of the rotating body 920 can help prevent stress concentration from occurring in the distal end 923*d* of the severing portion 923 by the distal tip of the severing portion 923 does not contact a lesion area and the distal end surface of the severing portion 923 can contact a lesion area while a treatment is performed on the lesion area. For this reason, the distal end surface of the severing portion 923 is hard to break.

In accordance with an exemplary embodiment, it can be preferable for the first tapered portion 913*b* to have, for example, a shape that forms the predetermined rake angle θ when seen from the side as illustrated in FIG. 29. Although the size of the rake angle θ is not particularly limited, it can be preferable, for example, that the rake angle θ is an acute angle.

Although the medical device according to the present disclosure is described through the embodiment and the modification examples hereinbefore, the present disclosure is not limited to only the content described in the embodiment, and can be changed as appropriate based on the scope of claims.

The body lumen as the target of various treatments using the medical device may be not only the blood vessel, but also, for example, a vessel, a ureter, a bile duct, a fallopian tube, or a hepatic duct.

For example, although an example in which the corrugated portions provided on the distal surface of the rotating body are configured as both of the corrugated severing portion and the abrasive portion is given in the description of the embodiment, the rotating body can be configured as at least one of the severing portion and the abrasive portion. In addition, in the rotating body, a corrugated portion such as a structure other than the severing portion and the abrasive portion may be provided on the distal surface of the rotating body.

In addition, for example, a shape, a thickness, a length, and a material for the rotating body are not particularly limited insofar as it is possible to apply a cutting force to the stenosed site. For example, the rotating body can have a trepanning edge surface (an annular edge surface having a thickness decreasing to the distal side) in the medical field. In a case of configuring the rotating body with the trepanning edge surface, the efficiency of cutting can be improved by forming the abrasive portion on a distal surface of the trepanning edge surface.

In addition, a structure of each portion or disposition of a member of the medical device described in the embodiment can be changed as appropriate, and the omission of use of an additional member described with illustration or also the use of another additional member can be performed as appropriate.

The detailed description above describes to a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for removing an object that exists in a body lumen, the medical device comprising:

a sheath configured to be inserted into the body lumen;

a drive shaft having a distal portion and a proximal portion, the drive shaft configured to extend through the sheath;

a rotatable hollow rotating body located on the distal portion of the drive shaft, and wherein a distal end surface of the rotating body has a concave-convex cut portion formed only between an inner distal end of the hollow rotating body and an outer periphery of the distal end of the hollow rotating body;

a guide wire lumen into which a guide wire is insertable in parallel with the sheath, the guide wire lumen being located on an outer surface of the sheath; and a connecting member disposed on an outer surface of the sheath and wherein the connecting member is disposed between the sheath and the guide wire lumen.

2. The medical device according to claim 1, wherein the guide wire lumen is indirectly or directly located on the outer surface of the sheath.

3. The medical device according to claim 1, further comprising:

a connection section located between the guide wire lumen and the rotating body.

4. The medical device according to claim 1, wherein a distal end of the guide wire lumen located distal to a distal end of the concave-convex cut portion.

5. The medical device according to claim 1, wherein the rotating body has a distal opening and a proximal opening.

6. The medical device according to claim 5, further comprising:

a center axis of the distal opening and a center axis of the drive shaft are in a same direction.

7. The medical device according to claim 1, comprising:

an area occupied by the distal end surface of the rotating body is greater than an area occupied by a hollow lumen of the rotating body.

8. A medical device for removing an object that exists in a body lumen, the medical device comprising:

a sheath configured to be inserted into the body lumen;

a drive shaft having a distal portion and a proximal portion, the drive shaft configured to extend through the sheath; and a rotatable hollow rotating body located on the distal portion of the drive shaft, and wherein a distal end surface of the rotating body includes a severing portion is formed between an inner circumference of the rotating body and an outer circumference of the rotating body, the severing portion including at least two different tapered portions, and each of the at least two different tapered portions includes a tapered portion on a distal side having an angle with respect to an axis in a longitudinal direction that is greater than an angle with respect to the axis in the longitudinal direction of a tapered portion on a proximal side.

9. The medical device according to claim 8, further comprising:

a guide wire lumen into which a guide wire is insertable in parallel with the sheath, the guide wire lumen being located on an outer surface of the sheath.

10. The medical device according to claim 8, wherein portions that form a concave-convex shape of the severing portion are arranged along a circumferential direction of the rotating body.

11. The medical device according to claim 8, wherein adjacent portions of a concave-convex shape of the severing portion form an acute angle.

12. The medical device according to claim 8, wherein a distal surface of the severing portion is perpendicular to an axis in a longitudinal direction of the medical device.

13. The medical device according to claim 8, comprising:

an outer circumference side portion of the severing portion are twisted in an opposite side of a rotation direction of an inner circumference side portion of the severing portion.

14. The medical device according to claim 8, further comprising:

a connecting member disposed on an outer surface of the sheath, and wherein the connecting member is disposed between the sheath and the guide wire lumen.

15. A medical device for removing an object that exists in a body lumen, the medical device comprising:

a sheath configured to be inserted into the body lumen;

a drive shaft having a distal portion and a proximal portion, the drive shaft configured to extend through the sheath;

a rotatable hollow rotating body located on the distal portion of the drive shaft, and wherein a distal end surface of the rotating body has a severing portion, the severing portion includes a plurality of concave-convex shaped notches arranged to be twisted in a circumferential direction of the rotating body on the distal end surface of the rotating body;

a guide wire lumen configured to receive a guide wire, the guide wire lumen being parallel to the sheath and arranged on an outer surface of the sheath;

an insertion member configured to be received within a lumen of the rotating body, the insertion member having a distal member having a distal surface having a crescent shape; and a breaking member that helically extends around the distal member, the breaking member being fixed to an inner surface of the rotating body.

16. The medical device according to claim 15, further comprising:

an area occupied by the distal end surface of the rotating body is greater than an area occupied by a hollow lumen of the rotating body.

17. The medical device according to claim 15, further comprising:

a connecting member disposed on an outer surface of the sheath, and wherein the connecting member is disposed between the sheath and the guide wire lumen.

18. The medical device according to claim 17, wherein the connecting member is a rod-like member.

* * * * *